(12) United States Patent
Rahman et al.

(10) Patent No.: US 11,717,181 B2
(45) Date of Patent: Aug. 8, 2023

(54) ADAPTIVE RESPIRATORY CONDITION ASSESSMENT

(71) Applicant: SAMSUNG ELECTRONICS CO., LTD., Gyeonggi-do (KR)

(72) Inventors: Md M. Rahman, San Jose, CA (US); Tousif Ahmed, San Jose, CA (US); Mohsin Ahmed, Sunnyvale, CA (US); Viswam Nathan, Mountain View, CA (US); Ebrahim Nematihosseinabadi, Santa Clara, CA (US); Korosh Vatanparvar, Santa Clara, CA (US); Jilong Kuang, San Jose, CA (US); Jun Gao, Menlo Park, CA (US)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 284 days.

(21) Appl. No.: 17/072,341

(22) Filed: Oct. 16, 2020

(65) Prior Publication Data
US 2021/0386318 A1    Dec. 16, 2021

Related U.S. Application Data

(60) Provisional application No. 63/037,736, filed on Jun. 11, 2020.

(51) Int. Cl.
*A61B 5/08* (2006.01)
*A61B 5/113* (2006.01)
*A61B 5/00* (2006.01)

(52) U.S. Cl.
CPC .......... *A61B 5/0816* (2013.01); *A61B 5/1135* (2013.01); *A61B 5/7221* (2013.01); *A61B 5/7225* (2013.01); *A61B 5/7285* (2013.01)

(58) Field of Classification Search
CPC ......... A61B 7/003; A61B 5/085; A61B 5/091; A61B 5/083; A61B 5/0833; A61B 5/0836;
(Continued)

(56) References Cited

U.S. PATENT DOCUMENTS 8,790,271 B2    7/2014   Jang et al.
10,506,976 B2   12/2019  Palley et al.
(Continued)

FOREIGN PATENT DOCUMENTS

CN    103118587 A    5/2013
CN    108113677 A    6/2018
(Continued)

OTHER PUBLICATIONS

Gu, C., & Li, C. Assessment of human respiration patterns via noncontact sensing using doppler multi-radar system. (2015). Sensors, 15(3), 6383-6398. (Year: 2015).*
(Continued)

*Primary Examiner* — Daniel L Cerioni
*Assistant Examiner* — Jonathan E. Cooper
(74) *Attorney, Agent, or Firm* — Cuenot & Forsythe & Kim, LLC

(57) ABSTRACT

Adaptive respiratory condition assessment can include capturing signals generated by sensors of a portable device positioned to sense a user's body. The sensors can generate the signals in response to sensor-detected movements of the user's body measured along multiple axes and corresponding to lung activity in the user's body during respiratory cycles. A preferred axis of measurement can be selected using signal processing performed by a signal processor embedded in the portable device. Waveforms generated from signals corresponding to signals generated in response to movements of the user's body measured along the pre-
(Continued)

ferred axis can be filtered for extracting biomarkers from the waveforms using the signal processor. The one or more biomarkers extracted correspond to the lung activity. Based on the biomarkers, a respiratory condition of the user can be determined. A notification based on the respiratory condition as determined can be generated and conveyed with the portable device.

17 Claims, 9 Drawing Sheets

(58) Field of Classification Search
CPC ............ A61B 5/087; A61B 2562/0219; A61B 5/6898; A61B 5/1135; A61B 5/113; A61B 5/6801; A61B 5/7221; A61B 2562/04; A61B 5/0507; A61B 5/0816; A61B 5/7225; A61B 5/7285; H04W 56/002
USPC ........................................................ 600/529
See application file for complete search history.

(56) References Cited

U.S. PATENT DOCUMENTS

| | | | | |
|---|---|---|---|---|
| 2010/0130873 | A1* | 5/2010 | Yuen | A61B 5/1126 600/595 |
| 2013/0184540 | A1 | 7/2013 | Boschetti et al. | |
| 2016/0029949 | A1* | 2/2016 | Landesberg | A61B 5/7278 600/534 |
| 2016/0282936 | A1* | 9/2016 | Larson | A61B 5/7221 |
| 2017/0010670 | A1* | 1/2017 | Tanaka | G06F 3/015 |
| 2018/0256096 | A1* | 9/2018 | Galeev | A61B 5/1123 |
| 2018/0358119 | A1* | 12/2018 | Bhushan | G16H 40/63 |
| 2019/0133499 | A1 | 5/2019 | Auerbach | |
| 2019/0282180 | A1 | 9/2019 | Babaeizadeh | |
| 2020/0086133 | A1 | 3/2020 | Wang et al. | |
| 2020/0170544 | A1 | 6/2020 | Aliverti et al. | |
| 2021/0000384 | A1* | 1/2021 | Jarchi | A61B 5/0816 |
| 2021/0105036 | A1* | 4/2021 | Chornenky | H04W 56/0035 |
| 2021/0275105 | A1* | 9/2021 | Peng | A61B 5/0205 |
| 2021/0345270 | A1* | 11/2021 | Murali | A61B 5/257 |

FOREIGN PATENT DOCUMENTS

| | | |
|---|---|---|
| KR | 101407946 B1 | 6/2014 |
| KR | 101725654 B1 | 4/2017 |
| WO | 2014150606 A1 | 9/2014 |
| WO | WO-2018185031 A1 * | 10/2018 ........... A61B 5/0205 |
| WO | 2018219030 A1 | 12/2018 |
| WO | 2021251587 A1 | 12/2021 |

OTHER PUBLICATIONS

WIPO Appln. No. PCTKR2021002114, ISR, dated Jun. 15, 2021, 3 pg.
WIPO Appln. No. PCTKR2021002114, WO, dated Jun. 15, 2021, 4 pg.

* cited by examiner

Capture, with a portable device, a plurality of signals generated by one or more sensors of the portable device positioned to sense a portion of a human user's body, wherein the one or more sensors generate the plurality of signals in response to sensor-detected movements of the user's body measured along multiple axes, the movements corresponding to lung activity in the user's body during one or more respiratory cycles
402

Select, using signal processing performed by a signal processor embedded in the portable device, a preferred axis of measurement from among the multiple axes
404

Filter, with the signal processor, waveforms generated by selected signals selected from among the plurality of signals, the selected signals corresponding to signals generated in response to movements of the user's body measured along the preferred axis of measurement
406

Extract from the waveforms, using the signal processor, one or more biomarkers corresponding to the lung activity
408

Determine a respiratory condition of the user based on the one or more respiratory markers
410

Generate notification based on the determined respiratory condition
412

Convey notification to the user via the portable device
414

FIG. 4

ADAPTIVE RESPIRATORY CONDITION ASSESSMENT

CROSS-REFERENCE TO RELATED APPLICATIONS

This application claims the benefit of U.S. Provisional Patent Application No. 63/037,736 filed on Jun. 11, 2020, which is fully incorporated herein by reference.

TECHNICAL FIELD

This disclosure relates to assessing and treating respiratory conditions in humans.

BACKGROUND

Respiratory ailments are a cause of much human suffering, as well as a significant public health concern. Respiratory ailments such as asthma, pulmonary fibrosis, cystic fibrosis, and chronic obstructive pulmonary disease (COPD), as well as infectious diseases of the lung such as COVID-19, cause or contribute to millions of deaths worldwide each year. Even the survivors of respiratory disease may require many days of hospitalization and lengthy, often expensive treatment. Respiratory disease is thus also a serious drain on countries' economies in terms of increased hospitalizations and lost workday productivity. A key to both identifying and treating respiratory conditions, as well as controlling the spread of respiratory infections, is regular respiratory assessment of humans—especially those with pre-existing conditions and those most susceptible to lung infection.

SUMMARY

In one or more embodiments, a method includes capturing, with a portable device, a plurality of signals generated by one or more sensors of the portable device positioned to sense a portion of a human user's body, the one or more sensors generating the plurality of signals in response to sensor-detected movements of the user's body measured along multiple axes and the movements corresponding to lung activity in the user's body during one or more respiratory cycles. The method can include selecting a preferred axis of measurement from among the multiple axes using signal processing performed by a signal processor embedded in the portable device. The method also can include filtering, with the signal processor, waveforms generated by selected signals selected from among the plurality of signals, the selected signals corresponding to signals generated in response to movements of the user's body measured along the preferred axis of measurement. Additionally, the method can include extracting from the waveforms, using the signal processor, one or more biomarkers corresponding to the lung activity. The method also can include determining a respiratory condition of the user based on the one or more biomarkers. The method further can include generating a notification based on the respiratory condition, as determined, and conveying the notification to the user with the portable device.

In one or more embodiments, a system includes a processor configured to initiate operations. The operations include capturing, with a portable device, a plurality of signals generated by one or more sensors of the portable device positioned to sense a portion of a human user's body, the one or more sensors generating the plurality of signals in response to sensor-detected movements of the user's body measured along multiple axes and the movements corresponding to lung activity in the user's body during one or more respiratory cycles. The operations can include selecting a preferred axis of measurement from among the multiple axes. The operations also can include filtering waveforms generated by selected signals selected from among the plurality of signals, the selected signals corresponding to signals generated in response to movements of the user's body measured along the preferred axis of measurement. Additionally, the operations can include extracting from the waveforms one or more biomarkers corresponding to the lung activity. The operations also can include determining a respiratory condition of the user based on the one or more biomarkers. The operations further can include generating a notification based on the respiratory condition, as determined, and conveying the notification to the user with the portable device.

In one or more embodiments, a computer program product includes a computer readable storage medium having instructions stored thereon. The instructions are executable by a processor to initiate operations. The operations include capturing, with a portable device, a plurality of signals generated by one or more sensors of the portable device positioned to sense a portion of a human user's body, the one or more sensors generating the plurality of signals in response to sensor-detected movements of the user's body measured along multiple axes and the movements corresponding to lung activity in the user's body during one or more respiratory cycles. The operations can include selecting a preferred axis of measurement from among the multiple axes. The operations also can include filtering waveforms generated by selected signals selected from among the plurality of signals, the selected signals corresponding to signals generated in response to movements of the user's body measured along the preferred axis of measurement. Additionally, the operations can include extracting from the waveforms one or more biomarkers corresponding to the lung activity. The operations also can include determining a respiratory condition of the user based on the one or more biomarkers. The operations further can include generating a notification based on the respiratory condition, as determined, and conveying the notification to the user with the portable device.

This Summary section is provided merely to introduce certain concepts and not to identify any key or essential features of the claimed subject matter. Other features of the inventive arrangements will be apparent from the accompanying drawings and from the following detailed description.

BRIEF DESCRIPTION OF THE DRAWINGS

The inventive arrangements are illustrated by way of example in the accompanying drawings. The drawings, however, should not be construed to be limiting of the inventive arrangements to only the particular implementations shown. Various aspects and advantages will become apparent upon review of the following detailed description and upon reference to the drawings.

FIG. 4 is a flowchart of an example method of adaptively assessing a human respiratory condition in accordance with one or more embodiments described herein.

DETAILED DESCRIPTION

Figure 1:
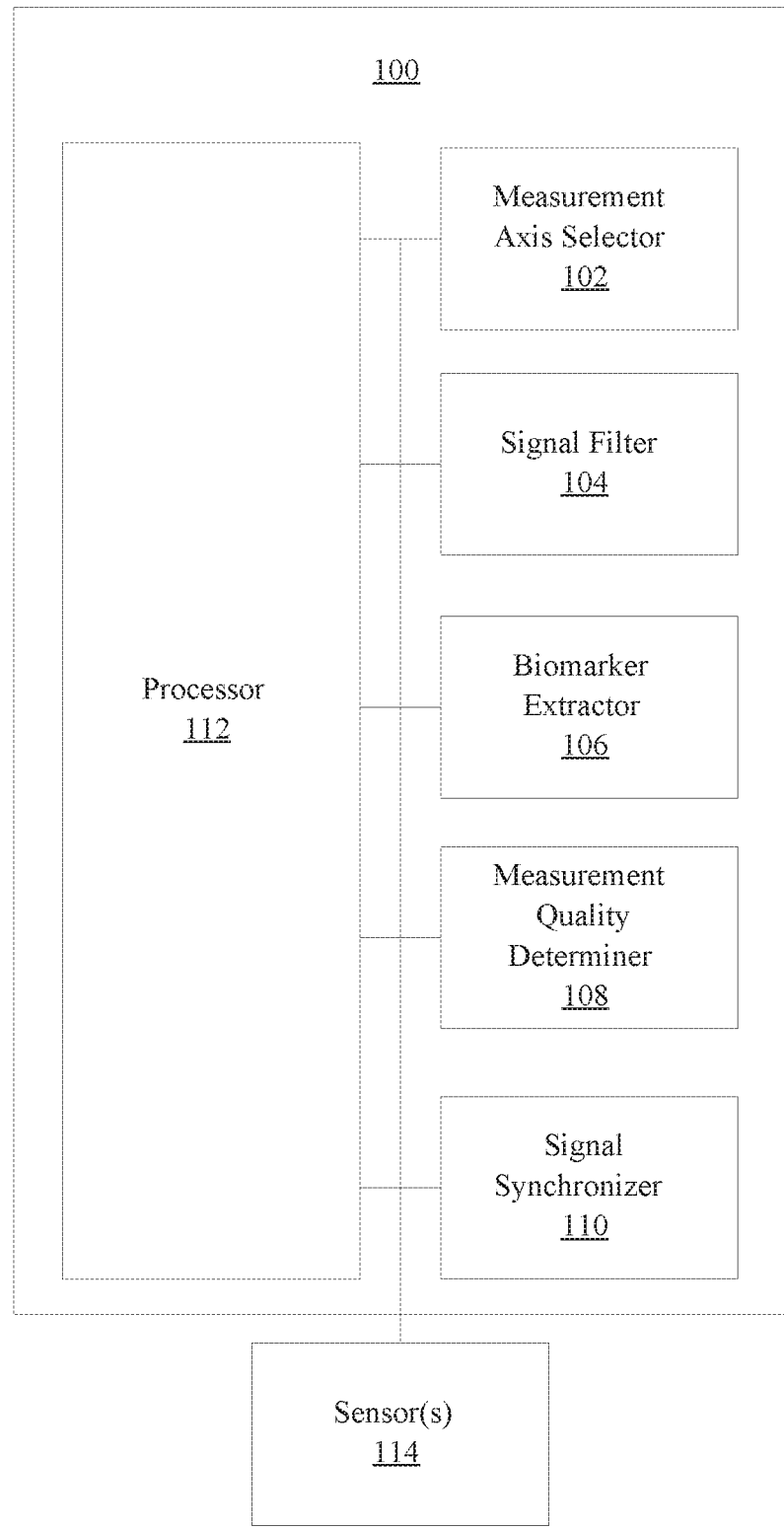
FIG. 1 illustrates an example system in accordance with one or more embodiments described herein.

While the disclosure concludes with claims defining novel features, it is believed that the various features described within this disclosure will be better understood from a consideration of the description in conjunction with the drawings. The process(es), machine(s), manufacture(s) and any variations thereof described herein are provided for purposes of illustration. Specific structural and functional details described within this disclosure are not to be interpreted as limiting, but merely as a basis for the claims and as a representative basis for teaching one skilled in the art to variously employ the features described in virtually any appropriately detailed structure. Further, the terms and phrases used within this disclosure are not intended to be limiting, but rather to provide an understandable description of the features described.

This disclosure relates to assessing and treating respiratory conditions in humans. Many existing types of methods and devices for assessing respiratory conditions in humans are expensive and cumbersome. Many such methods and devices require that an assessment be performed by a trained clinician in a hospital or clinical setting, at least in so far as necessary to ensure an accurate assessment of an individual's lung condition. This means that in many cases a necessary device for assessing an individual's lung condition may not be readily available when most needed by the individual. This is especially so under conditions such as the COVID-19 pandemic when an individual may, for public health reasons, be isolated at home. Certain methods or devices of assessing lung conditions, especially ones that require an individual's vigorous effort (e.g., spirometry), can cause or contribute to a flareup of a lung-impaired individual's condition (e.g., FEV1 greater than 15%). Thus, in a clinical setting the clinician may be forced to forego testing that requires a using a device or performing a procedure that may worsen the individual's condition. Perhaps even more concerning is the fact that an individual performing a test at home may not realize the danger and thus may worsen an underlying lung condition due to selecting an inappropriate test to perform or performing the test incorrectly.

The systems, methods, and computer program products illustrated by the embodiments described herein address these and other concerns and challenges related to assessing and treating human lung conditions.

Among the inventive aspects disclosed herein is assessing an individual's lung condition based on one or more biomarkers extracted from sensor-generated signals captured by one or more portable devices. As defined herein, a "portable device" is a handheld, wearable, or otherwise comfortably carriable device endowed with, or communicatively coupled to a device having, a processor for processing signals generated by one or more sensors in response to movements corresponding to lung activity in a user's body during one or more respiratory cycles. A portable device can be a smartphone or smartwatch, for example. A pair of earbuds communicatively coupled to a smartphone, for example, can be such a device.

As defined herein, a "biomarker" is a value (e.g., real number), measure, or other quantifiable indicator of a condition or state of a user's lung or the functioning thereof, the biomarker extracted from one or more signals captured by a portable device. An example biomarker is respiratory or breathing cycle, that is, one repetition of the three-fold pattern of inhalation (breathing air into the lungs), oxygen-carbon dioxide exchange, and exhalation (breathing air out of the lungs). Another example biomarker is respiratory or breathing rate, which is the rate at which breathing occurs, typically measured as breaths (breathing cycles) per minute (BPM). The ratio of inhalation to exhalation (I:E ratio) is another example biomarker. Still another example biomarker is fractional inspiratory time, defined herein as the ratio of inspiration time to total breath time.

"Extracting" a biomarker is defined herein as determining a value, measure, or other quantifiable indicator based on one or more underlying sensor-generated signals generated by lung activity in the user's body and captured by one or more portable devices. As defined herein, a signal is "captured" by receiving the signal with the portable device and storing the signal in a physical memory of the portable device either in the raw form in which the signal is received or as data structured for processing the signal (as received or as a data structure) by a processor of the portable device. Relatedly, as also defined herein, signals may be "fused" by combining two or more signals to generate data whose structure is processable by the processor for generating one or more biomarkers based on the signal combination.

One or more biomarkers extracted from signals captured by a user's portable device can be used to determine a lung condition of the user. In certain embodiments, the biomarkers are input as elements of a feature vector into a machine learning model operating on a processor of, or accessible via a network connection to, the portable device. The machine learning model can be trained (e.g., using clinical data) to classify lung conditions based on a feature vector input comprising one or more extracted biomarkers. Based on the specific biomarkers, the model can classify the user's lung condition as healthy or unhealthy. Using a multi-classification model, for example, the model can classify the likely cause and/or severity of an unhealthy lung condition.

An innovative aspect of the embodiments disclosed herein is the synchronizing of multiple signals captured by separate devices. The synchronizing enables a device to distinguish between machine-based signal misalignment (e.g., clock drift) and signal differences engendered by an unhealthy lung condition (e.g., phase difference in thoracic breathing pattern versus abdominal breathing pattern). For example, in some embodiments, signals generated by thoracic breathing movements are captured by the inertial measurement unit (IMU) of a smartphone held against a user's chest. Simultaneously, abdominal movements corresponding to the user's breathing are captured by the IMU of a smartwatch held against the user's abdomen. The signals captured by the separate devices may be misaligned, for example, by drift in the respective clocks of the devices. In order to accurately assess lung condition, the signals should be properly aligned by removing drift. However, it is critical that the aligning not obscure an actual difference between different measurements of breathing patterns, differences that can indicate a serious lung condition.

For example, thoraco-abdominal synchrony is a biomarker which measures the degree to which motion of a user's ribcage parallels motion of the user's abdomen while breathing. Lack of synchrony between the thoracic and abdominal motion while breathing (asynchronous breathing) is an indicator of various types of respiratory disorders and/or respiratory muscle dysfunctions and is clinically assessed as a sign of respiratory distress and increased effort of breathing. Among the innovative aspects of the embodiments disclosed herein are certain signal processing techniques, implemented in processor-executable software and/or dedicated circuitry, that remove machine-based misalignment of signals simultaneously captured by separate devices—effecting alignments necessary for accurately fusing the signals—while still preserving non-machine-related differences (e.g., phase-based asynchrony) that can indicate an actual underlying lung condition.

Another innovative aspect of the embodiments disclosed herein is estimating the measurement quality of the biomarkers extracted from captured signals (individual and/or synchronized). The measurement quality provides an indication of the reliability of the extracted biomarkers for determining the respiratory condition of a user. Measurement quality can also provide an indication of accuracy achieved with the above-described process of synchronizing separately captured signals.

Still another innovative aspect is determining a likely reason for an estimated quality measure that is below a predetermined acceptable quality level. Specifically, the determination is made as to whether the reason is likely due to a possible adverse lung condition of the user, or likely due to a user wrongly using one or more portable devices to effect the capture of signals from which the biomarkers are extracted, or possibly due to a failure of one or more components of the portable device(s). The ability to estimate a quality of results not only enhances accuracy of the lung condition determination based on extracted biomarkers, but also enhances the functioning of the underlying devices. The performance of the underlying devices is improved by avoiding re-measurements that, due to user mishandling or component failure of a device, are likely to waste processing resources without achieving reliable results if further measuring is done using the device.

Yet another inventive aspect disclosed herein is determining a likelihood, based on an initial determination of a user's lung health, that the user can perform a subsequent confirmatory test to confirm the initial determination. The likelihood can reflect a likelihood that the user can successfully perform the confirmatory test without an inordinate danger (with a predetermined confidence level) of a flareup in an underlying lung condition revealed by the initial determination. Additionally, instructions can be provided to the user via a user interface of the portable device instructing the user on the proper way to perform the confirmatory test.

Still another inventive aspect is passive monitoring for sounds (e.g., cough, wheezing, shortness of breath) with a microphone or other acoustic signal transducer embedded in a device worn by the user (e.g., earbuds). For example, a microphone embedded in one of a pair of earbuds can capture such signals. The earbuds can communicatively couple to a smartphone that is able to perform signal processing on the signals. The smartphone can incorporate a model trained using machine learning to recognize certain sounds (e.g., cough, wheezing, shortness of breath) indicating a potential adverse lung condition. In response the smartphone, via a user interface, can notify the user of the need to perform one or more breathing tests or to seek medical attention.

Further aspects of the embodiments described within this disclosure are described in greater detail with reference to the figures below. For purposes of simplicity and clarity of illustration, elements shown in the figures have not necessarily been drawn to scale. For example, the dimensions of some of the elements may be exaggerated relative to other elements for clarity. Where considered appropriate, reference numbers are repeated among the figures to indicate corresponding, analogous, or like features.

Figure 7:
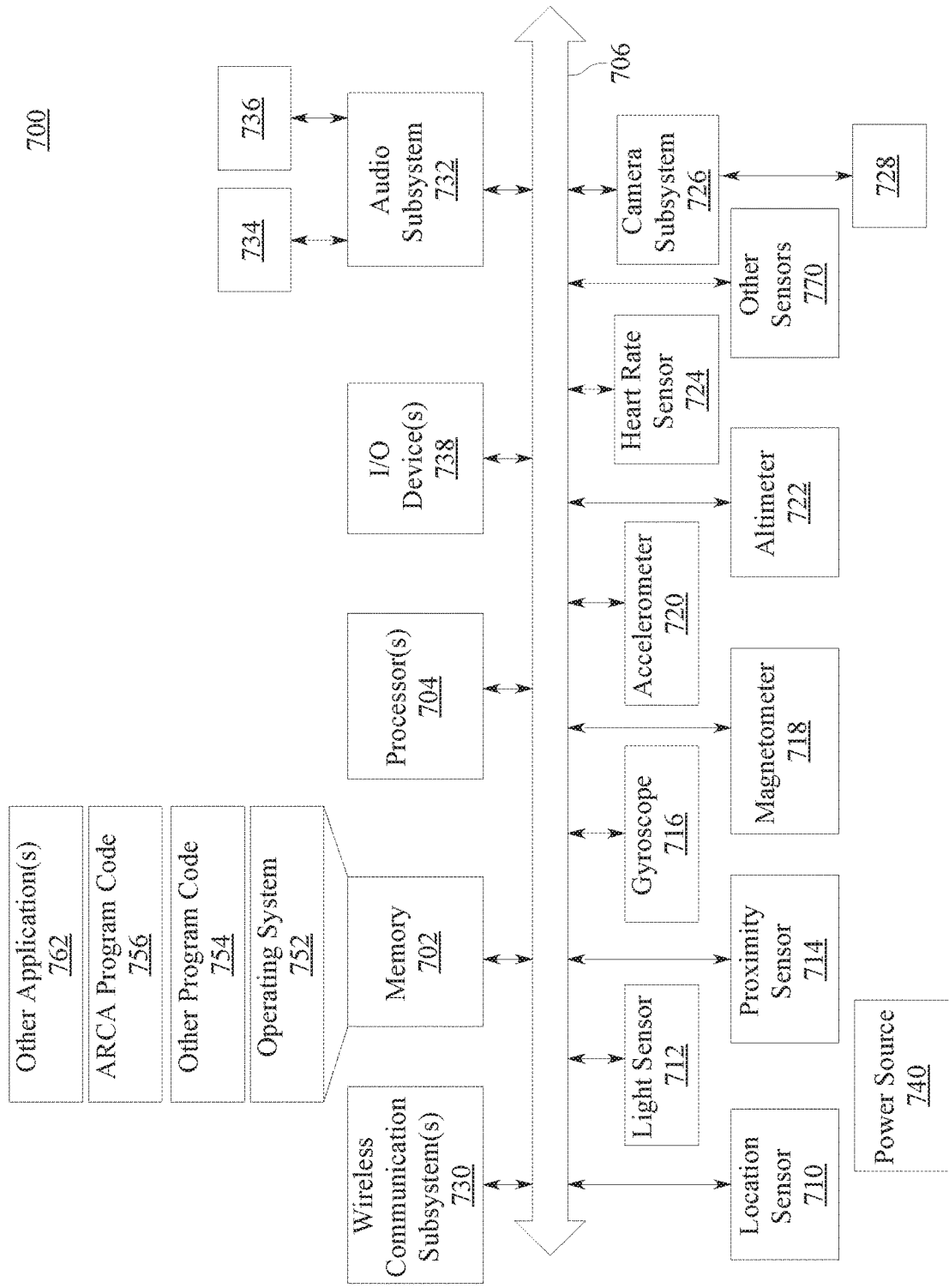
FIG. 7 illustrates an example portable device in which a system for adaptively assessing a human respiratory condition is implemented in accordance with one or more embodiments described herein.

FIG. 1 depicts adaptive respiratory condition assessor (ARCA) 100, according to an embodiment. ARCA 100 can be implemented in a portable device (e.g., smartphone, smartwatch) such as example portable device 800 described in detail with reference to FIG. 8. The portable device is endowed with one or more processors and one or more sensors (e.g., IMU) for sensing movement of a user's body, the movements corresponding to lung activity in the user's body (e.g., thoracic extension) during one or more respiratory cycles of the user. The portable device can additionally include one or more of the other components, such as those shown in the context of portable device 700 (FIG. 7). In various embodiments, ARCA 100 can be implemented in software that is executable on a processor of the portable device and can be stored in a memory of the portable device. In other embodiments, ARCA 100 can be implemented in circuitry integrated in the portable device. ARCA 100, in still other embodiments, can be implemented in a combination of software and dedicated circuitry. In some embodiments, ARCA 100 performs the operations described herein using a single portable device (e.g., smartphone). In other embodiments, ARCA 100 performs the operations using multiple devices (e.g., smartphone communicatively coupled to a pair of earbuds or smartwatch). For example, in some embodiments, the portable device comprises a device (e.g., smartphone) that receives signals (via wireline or wireless connection) from sensors embedded in one or more peripheral devices (e.g., smartwatch, earbuds). A smartphone, smartwatch, earbuds, and microphone-embedded neckband are but some of the devices that can serve as portable devices and/or peripheral devices operating singly and in various combinations with one another for performing the operations described in the various embodiments disclosed herein.

ARCA 100 illustratively includes measurement axis selector 102, signal filter 104, and biomarker extractor 106. Illustratively, ARCA 100 includes processor 112 of a portable device, and each of measurement axis selector 102, signal filter 104, and biomarker extractor 106 comprise software modules storable in a memory (not shown) of the portable device and executable by processor 112. The operations performed by ARCA 100 are performed on signals captured by one or more sensors 114 of the portable device.

Figure 2A:
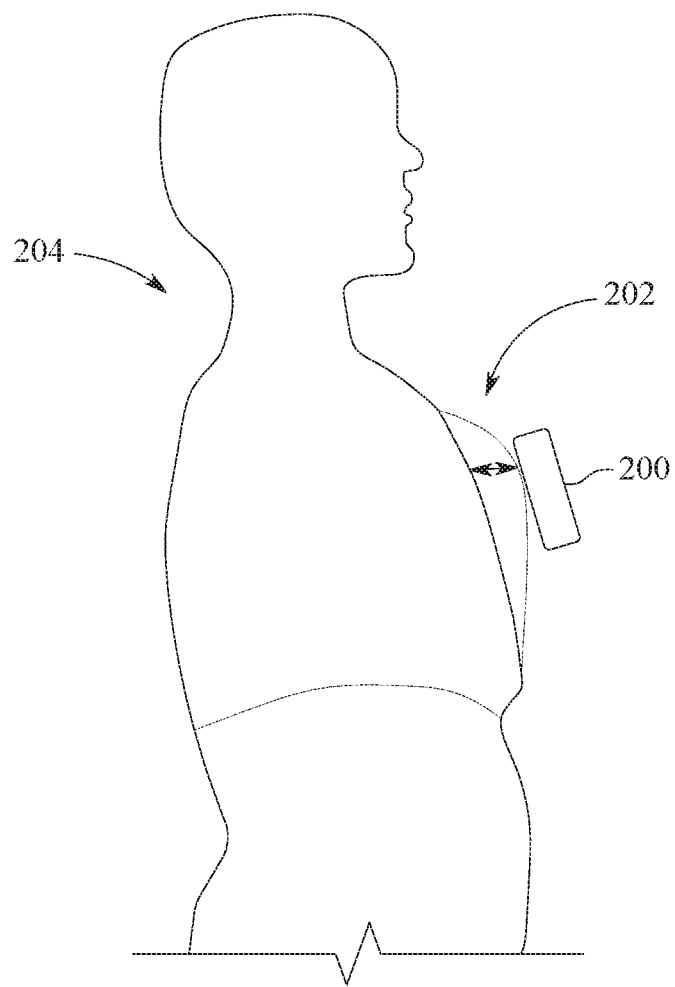
FIGS. 2A-2C illustrate the capture of signals from which biomarkers are extracted in accordance with one or more embodiments described herein.
Figure 2B:
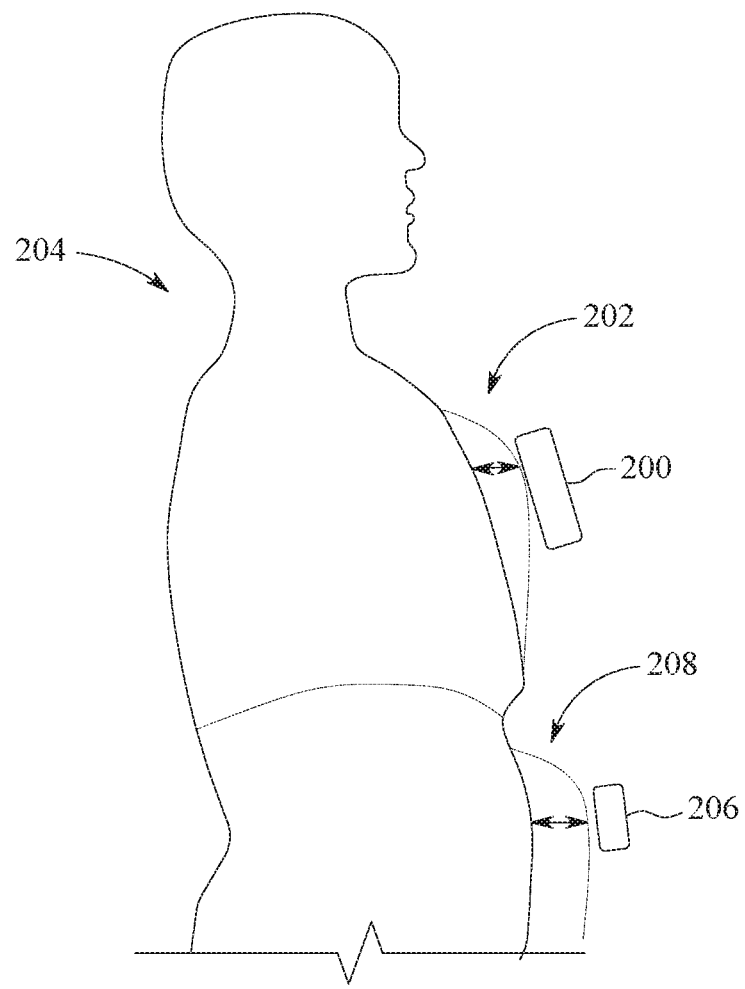
Figure 2C:
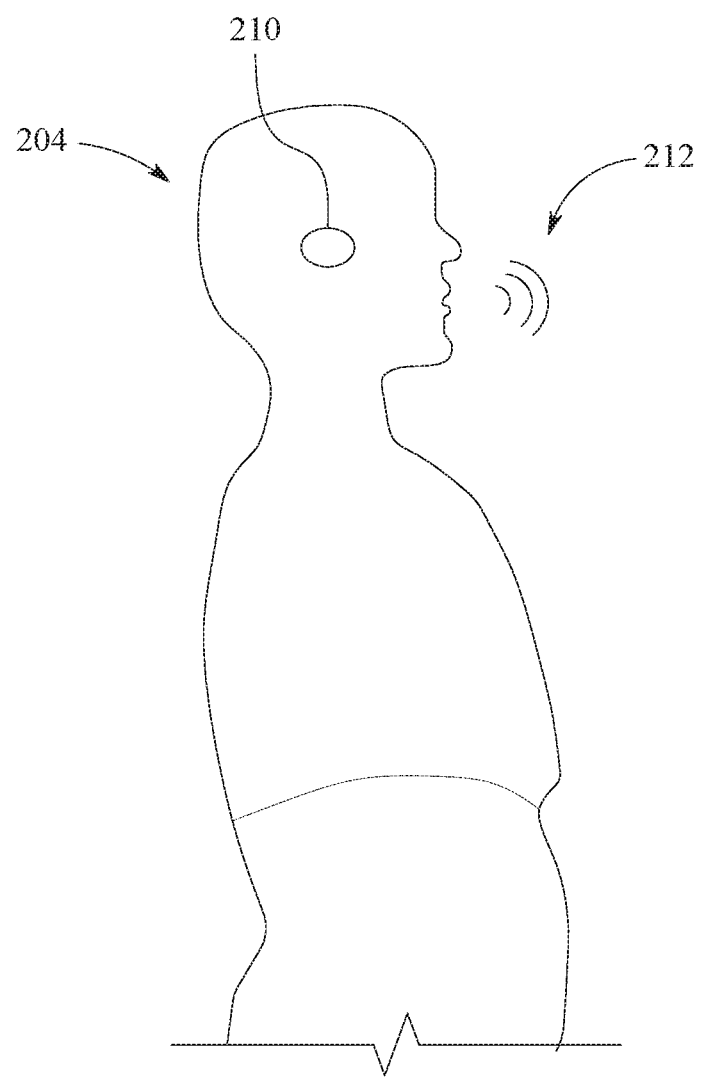

Sensor(s) 114 can sense movements in portions of a human user's body, the movements corresponding to lung activity in the user's body during one or more respiratory cycles. For example, a smartphone in which ARCA 100 is implemented can include one or more inertial measurement units (IMUs) or other microelectromechanical (MEM) sensors capable of sensing movements corresponding to lung activity. Referring additionally to FIG. 2A, ARCA 100 is illustratively implemented in smartphone 200, which captures signals generated by an IMU (not shown) of the smartphone as the smartphone is held against thoracic region 202 of user's body 204. Alternatively, in FIG. 2B, smartphone 200 additionally captures signals generated by an IMU (not shown) of smartwatch 206 communicatively coupled to smartphone 204. Smartwatch 206 is held against user's abdominal region 208 for simultaneously capturing signals generated by abdominal movements during the lung activity. In still another arrangement, shown in FIG. 2C, smartphone 200 is communicatively coupled to earbud 210 having an IMU (not shown) that can detect motions of the user's head and, optionally, an embedded microphone for capturing acoustic signals 212 generated in response to the user breathing, coughing, and/or speaking.

Each of the various IMUs, for example, can combine a triaxial accelerometer (three orthogonally arranged accelerometers) and a triaxial gyroscope that can communicate with a microcontroller or other integrated circuit within the smartphone, smartwatch, and/or earbuds for rapid data exchange and low power consumption. Such sensors can be configured with high sensitivities. For example, a gyroscope full-scale range is ±250°/s. With 16-bit analog-to-digital converter (ADC), the sensitivity can be calculated as 250/215=0.0076°/s. Similarly, the sensitivity of accelerometer can be calculated as 2 g/215=61 µg.

Referring still to FIG. 1, sensor(s) 114 (e.g., smartphone IMU, smartwatch IMU, earbud IMU) generate a plurality of signals in response to detecting movements in the user's body, the movements corresponding to lung activity in the user's body during one or more respiratory cycles. Measurement axis selector 102 selects a preferred axis of measurement (e.g., one axis selected from a six-axis IMU comprising a triaxial accelerometer and triaxial gyroscope based on signal generated by each, or a nine-axis IMU that in addition to the accelerometer and gyroscope also includes a triaxial magnetometer). The preferred axis of measurement is selected by measurement axis selector 102, executing on processor 112. Measurement axis selector 102 performs signal processing to identify a signal waveform having maximum periodicity. The waveform having maximum periodicity is one having the maximum amplitude observed within a predetermined frequency range (e.g., 0.13 Hz to 0.66 Hz, corresponding to between 8 and 40 breaths per minute, respectively). In some embodiments, maximum periodicity is determined by measurement axis selector 102 performing real time signal processing using Fourier transformation.

Signals corresponding to signals generated in response to movements of the user's body measured along the preferred axis of measurement can be selected from among the multiple signals captured. The selected signals are those whose waveforms corresponding to signals that measurement axis selector 102 determines are ones that exhibit the maximum periodicity. Signal filter 104, also executing on processor 112, performs real time signal processing on the selected signals. Signal filter 104 detects "peaks" and "valleys" (maxima and minima, respectively) in the signal waveforms while eliminating spurious peaks according to one or more procedures described below.

In some embodiments, a respiration cycle (a complete cycle of inhalation and exhalation) of the user is estimated from the selected signals, which are generated in response to sensor-detected expansion and contraction of the user's thoracic region and filtered with signal filter 104 implemented as a Savitzky-Golay filter. The Savitzky-Golay filter fits a polynomial to a set of samples and evaluates the resulting polynomial at a single point of the set within an approximation interval, yielding a result equivalent to discrete convolution with a fixed impulse response. Based on the principle of local least-squares polynomial approximation, the Savitzky-Golay filter can be used to smooth noise-infused data but offers the advantage of preserving peaks. By signal filter 104 applying a Kalman filter as a post-processor, in certain embodiments, the signals generated in response to the respiratory cycles of the user can be accurately identified, possibly with a mean absolute error of less than one breath per minute.

The corresponding signal waveform peaks and valleys are determined by signal filtering performed by signal filter 104. In some embodiments, signal filter 104 initially performs signal smoothing using a moving average filter of M points. The signal waveforms typically oscillate more in the presence of user exertion (e.g., walking rather than sitting or standing). Irregular oscillation unrelated to the user's breathing can also be caused by the manner that the user handles the portable device in capturing signals to measure the user's breathing, causing spurious peaks, for example. Signal smoothing by signal filter 104 can eliminate or reduce spurious peaks, though too large a value of M can contribute to over-smoothing thereby reducing the detectability of relevant peaks and valleys. Therefore, M can be set to balance the proportion of correctly identified cycles against reductions in amplitude due to smoothing. In some embodiments, M is iteratively tuned based on clinical data. For example, an appropriate value of M can be 5 (250 ms) for sitting and standing signals, and 11 (515 ms) for walking.

Following signal smoothing, signal filter 104 can generate a moving average centerline (MAC) adjusted to intercept each respiratory cycle twice (once in the inspiration phase and again in the expiration phase of the user's breathing) over an average respiratory cycle duration. The average respiratory cycle duration can be adjusted using clinical data to mitigate baseline drift. Signal filter 104 can identify points where the MAC curve intercepts the smoothed signal waveform, determining both an "up" intercept, $I_{up}$, and a "down" intercept, $I_{dn}$. $I_{up}=y(t-1) \leq MAC(t) \leq y(t)$, where y(•) corresponds to signal amplitude at time t. $I_{dn}=y(t-1) \geq MAC(t) \geq y(t)$. Ideally, there is one up intercept and one down intercept for each user respiratory cycle. In response to more than one pair of intercepts appearing in the signal waveform, signal filter 104 can eliminate spurious intercepts. If a signal waveform yields more than two consecutive intercepts with the same label (e.g., up/down), signal filter 104 retains the last one and discards the previous one. Using the procedure, signal filter 104 generates the sequence $I_{dn}(1) < I_{up}(1) < I_{dn}(2) < I_{up}(2) \ldots < I_{dn}(n) < I_{up}(n)$, where n is the number of up (down) intercepts. Signal filter 104 determines a signal waveform peak, which corresponds to the onset of expiration of a respiratory cycle, by determining the maximum between consecutive up and down intercepts, determined as $peak(i)=\max(y(I_{up}(i)):y(I_{dn}(i+1)))$, where i=1, 2, . . . , p (p being the number of peaks).

During a user's respiratory cycle, determining the signal waveform maxima and minima typically yield the correct time-demarcation points of the user's inhalation and exhalation of a respiratory cycle. In certain situations, however, the user's breathing can be non-rhythmic (e.g. when the user is speaking) or even erratic. A maximum peak may not correctly reflect the user's breathing pattern. Signal filter 104 can detect such irregularities by identifying one or more "notches" (defined herein as waveform points bookended between a sharp rise and fall) within a predetermined neighborhood or region of an identifiable peak. Signal filter 104 can make a needed adjustment by initially treating each of one or more maxima among all the notches as a candidate peak. Signal filter 104 identifies a maximum (within a neighborhood) from among the candidates. A candidate is identified as the maximum if a predetermined percentage (e.g., 70%) of inspiration of a respiratory cycle is complete by the time that the candidate maximum occurs within the signal waveform.

In the event that the MAC line fails to intersect small cycles at the maximum, there is a possibility that there exists another cycle within the respiratory cycle, thus shifting the peak may be insufficient. Therefore, signal filter 104 identifies a portion within the respiratory cycle determined to be likely to accurately correspond to the actual respiratory cycle. That is, the relevant portion exhibits ascending and descending trends consistent with inspiration and expiration phases of a respiratory cycle. Signal filter 104 splits the identified cycle in two and identifies the relevant points within each. If both cycles' inspiration and expiration durations are greater than a predetermined time (e.g., 0.4 seconds) and the total cycle duration lies within a predetermined range (e.g., 0.8 seconds to 12.5 seconds), signal filter 104 identifies both cycles as valid cycles. Any newly formed cycles (created by the splitting) that do not meet the criteria are ignored and signal filter 104 determines that only one cycle is accurate, adjusting the position of the peak as necessary. If none meet the criteria, no reliable results are obtained. ARCA 100 can optionally generate a message, conveyed by the portable device to the user, instructing the user to perform a selected breathing test in attempting to obtain reliable results.

Signal filter 104 determines the start and end of the user's respiratory cycle by identifying signal waveform valleys. Specifically, a valley is a waveform minimum that occurs between a down intercept and subsequent up intercept corresponding to a semi-sinusoidal respiratory cycle. If a cycle has an expiratory pause, however, the minimum may not represent the actual valley. Therefore, signal filter 104 treats such a minimum as a candidate valley and, advancing from the candidate valley to the next up intercept, computes intervening slopes. By examining the slopes, signal filter 104 determines the point from which the signal waveform monotonically rises towards the next peak and accepts that as the actual valley. If the amplitude of the signal waveform changes substantially, the MAC may not intersect a respiratory cycle. For example, if the baseline shifts abruptly or there lies a small cycle adjacent to a larger one, a moving average may not adequately cope with the change such that no relevant point is determinable by signal filter 104. Accordingly, signal filter 104 seeks a portion within a cycle that is a candidate for the respiratory cycle, detecting relevant points corresponding to the new cycle and accepts both cycles as valid cycles.

Signal filter 104 screens peaks and valleys occurring in the signal waveform. In searching for peaks and valleys, signal filter 104 accepts only those temporally separated by a predetermined time interval. The predetermined time interval, for example, can be one that is more than 0.4 seconds, from a peak to the next valley or from a valley to the next peak, assuming that the minimum breathing period is around 0.8 s. Signal filter 104 discards the peaks and valleys that occur within a shorter duration as spurious. Additionally, if an inspiration or expiration amplitude is too small (e.g., 10% or less of the mean cycle amplitude), signal filter 104 determines the associated cycle to be of insufficient quality and screens out the cycle.

Biomarker extractor 106 extracts biomarkers from the selected signals. Extracted biomarkers can include respiration rate, FEV1 (forced expiratory volume in one second), and fractional inspiratory time, for example. In certain embodiments, ARCA 100 can fuse these biomarkers with multiple other biomarkers for determining one or more respiratory conditions of the user using other signals sensed by the portable device or a peripheral device connected thereto. For example, photoplethysmography (PPG) can be performed using a smartphone's white light-emitting diode as light source and phone camera as photodetector. When ARCA 100 is implemented in such a device that includes or is communicatively coupled with a device capable of performing other assessments, such as PPG, the extracted biomarkers can be fused with other biomarkers such as heart rate, heart rate variability, oxygen saturation (SpO2), and other such biomarkers. Moreover, as also described below, ARCA 100 can align signals separately captured by different devices to ensure the accuracy of the extracted biomarkers.

Biomarker extractor 106, in certain embodiments, extracts biomarkers based on the onset and end of each respiratory cycle indicated by waveform maxima and minima, again, identified as peaks and valleys in the waveforms. Biomarker extractor 106, in some embodiments, determines the user's respiration rate or breathing frequency, $rr_t^s$, as $$rr_t^s = 60 \times \underset{0.1 \leq f \leq 0.5}{\mathrm{argmax}}\, FFT_t^s(f), \text{ where}$$

$$FFT_t^s(f) = \left| \sum_{i=t-w}^{t} s_i^b \times e^{-j2\pi fi/w} \right|$$

Breathing frequency of the user can be converted to respiratory cycle duration, $T_{total}$, by taking the inverse of the user's respiration rate or breathing frequency, $rr_t^s$: $T_{total}=1/rr_t^s$. Peak detection is applied and spurious peaks removed (as described above) to ensure that peak-to-peak time is greater than $c_1 * T_{total}$ and valley-to-peak amplitude is greater than $c_2 * A_m$, where $c_1$ and $c_2$ are predetermined constants (e.g., based on clinical data), $A_m$=median($r_1$, $r_2$, ... $r_n$), $r_i$=|peak$_i$–valley$_i$|, and n is the number of (peak, valley) pairs.

Figure 3:
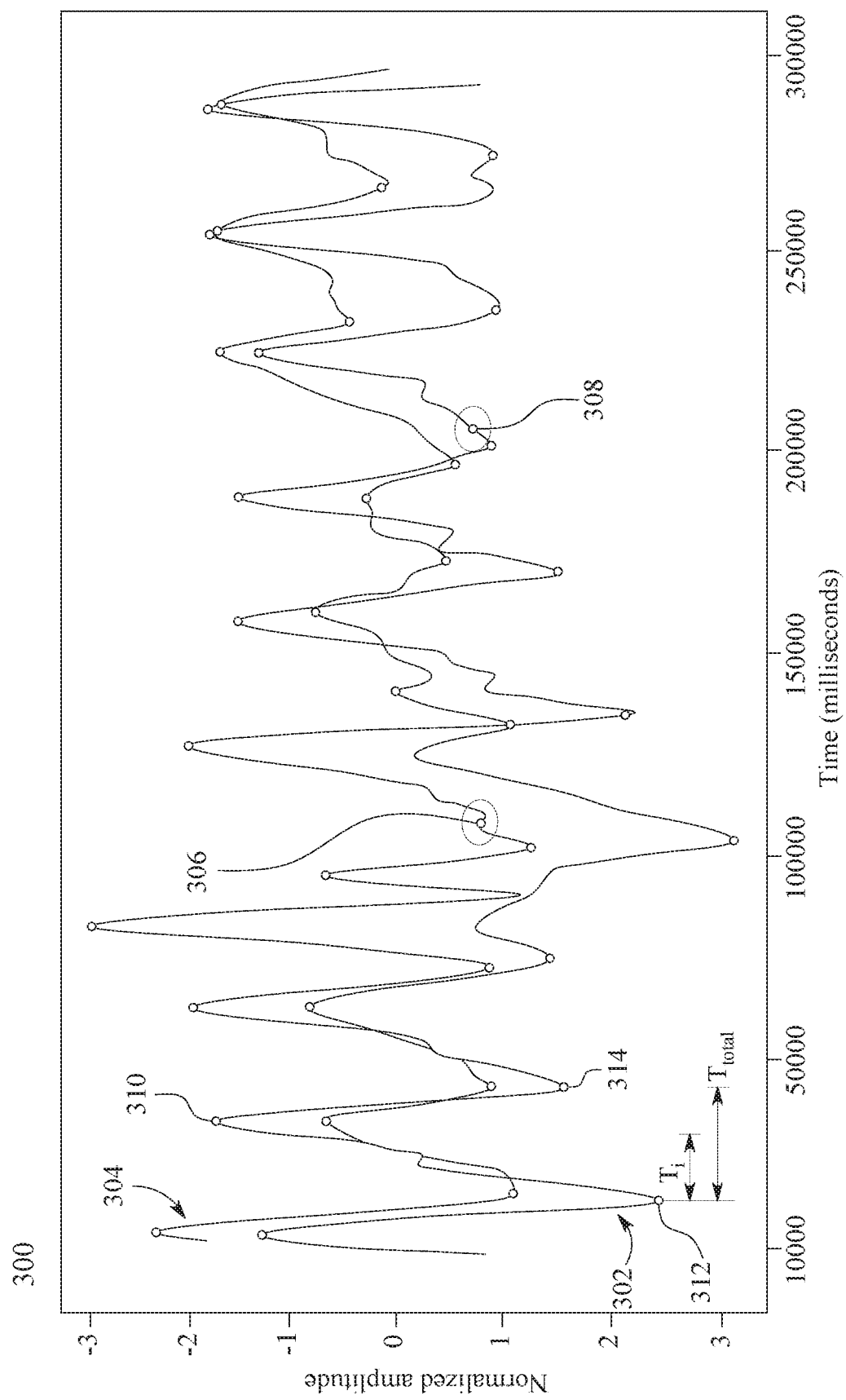
FIG. 3 illustrates example waveforms simultaneously captured by separate devices for adaptively assessing a human respiratory condition in accordance with one or more embodiments described herein.

FIG. 3 depicts graph 300 of two example signal waveforms, aligned according to the procedures described below, in which the signal amplitudes are normalized and time is measured in milliseconds. Signal waveform 302 corresponds to signals captured by a smartphone. Signal waveform 304 corresponds to signals captured by a smartwatch. The above-described processes can detect peaks and valleys (maxima and minima) of both signal waveforms, including spurious peak 306 and spurious peak 308 in signal wave form 302.

One biomarker that may be extracted by biomarker extractor 106 is fractional inspiratory time. Fractional inspiratory time, in FIG. 3, is computed as $T_i/T_{total}$, where Ti=Time(peak$_i$ 310)–Time (valley$_i$ 312), and $T_{total}$=Time (valley$_{i+1}$ 314)–Time(valley$_i$ 312), that is, the ratio of the inspiratory duration over the total duration of a respiratory cycle.

ARCA 100 determines a respiratory condition of the user based on one or more of the biomarkers extracted by biomarker extractor 106. A respiratory condition can be determined by ARCA 100 based on processing, with processor 112, the data corresponding to one or more extracted biomarkers. In processing the data, ARCA 100 compares a current biomarker to a baseline value. The baseline, in certain embodiments, is clinically determined based on a statistically valid sample of subjects. In other embodiments, the baseline uniquely corresponds to a specific user and is determined by ARCA capturing and storing separate measures of the user's lung activity over time. With respect to the above-described fractional inspiratory time, for example, a reduction of the fractional inspiratory time relative to the baseline can indicate a worsening COPD or asthmatic condition. Moreover, in processing the data ARCA 100 can identify a lung condition of the user based on detected changes in one or more biomarkers extracted between $t_1$ and $t_0$. Changes in a biomarker can indicate a respiratory condition of the user, in certain cases even prior to the user exhibiting any external symptoms observable by a physician or trained clinician.

In certain embodiments, ARCA 100 fuses two or more biomarkers. For example, ARCA 100 can fuse the user's respiratory rate, fractional inspiratory time, and other biomarkers with heart rate, oxygen saturation (SpO2), and other biomarkers collected at the same time using multiple sensors (e.g., IMU, PPG) of the portable device or embedded in other devices communicatively coupled to the portable device. In some embodiments, the biomarkers can be fused by ARCA 100 as elements of a feature vector for input into a machine learning model trained using sample data collected in a clinical setting. The machine learning model can be trained—for example, as a multi-layer deep learning model—to classify the user's lung condition. Based on the input feature vector the model can enable ARCA 100 to classify the user's lung condition as healthy or unhealthy. If unhealthy, depending on the training of the machine learning model used by ARCA 100, the user's lung condition can be assessed further to indicate a likely cause of the unhealthy condition. In some embodiments, ARCA 100 can operate on a portable device capable of storing and generating results based on the model. In other embodiments, ARCA 100 can use a network connection of the portable device to convey (e.g., wirelessly) the input feature vector and receive the machine learning model-determined classification. ARCA 100 can use a user interface of the portable device to convey the classification to the user.

ARCA 100, as described, can process multiple signals captured by one or more communicatively coupled portable devices and corresponding to different axes of measurements. Measurement axis selector 102 selects the preferred axis based on the respective periodicity of each signal's waveform, the preferred axis having maximum periodicity, as described above. A maximum periodicity can be determined using different processes. For example, measurement axis selector 102 can determine the maximum periodicity in a signal waveform using Fourier transformation (FFT) or based on a maximum signal-to-noise ratio determination.

In some embodiments, ARCA 100 optionally includes measurement quality determiner 108 to estimate the quality of the biomarkers extracted by biomarker extractor 106 based on a comparison of different values of a biomarker obtained when the preferred axis of measurement is determined using different processes (e.g., FFT and signal-to-noise ratio). ARCA 100, in one embodiment, for example, extracts a biomarker—namely, the user's respiratory frequency, $rr_s^t$—by applying different procedures: (1) a Fourier transformation and (2) a signal-to-noise ratio determination. In an ideal case, both procedures select the same axis and extract the same estimated value of the biomarker, $rr_s^t$. There are instances in which multiple axes provide similar information regarding a breathing parameter estimation. In some instances, the separately determined biomarkers, though not identical, are sufficiently close to each other and are within a valid respiratory range. The less the difference in values, the more likely the values of the extracted biomarker are accurate.

Measurement quality determiner 108 quantifies the accuracy or reliability of extracted biomarkers. In some embodiments, measurement quality determiner 108 determines a measurement quality based on a tunable quality indicator, defined as clinically acceptable difference (CAD)=$[-c, c]$, which varies based on the detection sensitivity of a device capturing signals and which is derived from clinical measurements made under controlled conditions. For example, to measure the quality of a biomarker whose values measure the user's respiratory rate in breaths per minute (BPM), measurement quality determiner 108 can use a CAD of $[-c, c]$ BPM, where c is determined by the percentage of accurate measurements made on patients in a clinical setting.

In one embodiment, measurement quality determiner 108 determines the measurement quality using an agreement-based procedure, which yields a probability $\theta$ of measurement agreement with respect to a CAD. The probability is measured as:

$$\theta(s) = P(|Y_{i2} - Y_{i1}| c | S_i = s),$$

where $S_i$ is the true measurement of a biomarker for subject i, which is assumed to be normally distributed with mean $\mu$ and variance $\sigma_s^2$, $S_i \sim N(\mu, \sigma_s^2)$, and where $Y_{i1}$ and $Y_{i2}$ are different measurements of the same biomarker as by determined by ARCA 100. The probability, $\theta$, provides a quantitative measure of the likelihood that the absolute difference between the differently estimated biomarker values as estimated by ARCA 100 are within the CAD, given that the true measurement is s. If the probability meets or exceeds a predetermined threshold (e.g., 95%), the measurement quality determiner 108 accepts the quality of the measurement of the biomarker. Otherwise, the measurement is rejected. Optionally responses of ARCA 100 in the face of a rejected measurement are described below.

In another embodiment, measurement quality determiner 108 determines the measurement quality using a frequency component-based method. The frequency component-based procedure estimates the measurement quality using a frequency spectrum distribution. The estimate is based on the following quality metric:

$$q_t^s = \frac{kurt(FFT_t^s(f))}{kurt(p_{rr_t^s})}, \, \forall f \in [f_{min}; f_{max}],$$

which provides a measure of "signal purity" (defined herein as a quantitative measure of the degree to which a signal is uninfused with noise) of a respiratory signal spectrum. The less noise-infused the signal, the more sinusoidal the signal waveform. The waveform of a resting respiratory signal free of noise is almost a sinusoidal signal, with a spectrum having a single frequency component corresponding to an individual's breathing frequency. A noise-infused signal, by contrast, exhibits a spectrum that additionally includes other frequency components.

The frequency component-based method compares a noise-infused signal spectrum with a noise-free signal spectrum. The noise-infused signal spectrum is more diffused, corresponding to greater kurtosis (or "fatter tails"), whereas the noise-free resting respiratory signal spectrum is more concentrated in a single neighborhood, corresponding to lower kurtosis (or "thinner tails"). The spectra correspond to signals used to estimate a biomarker, namely, respiratory rate. Quality metric $q_t^s$ provides a measure of signal purity for a given estimate of a user's respiratory rate, $rr_t^s$, by taking the ratio of the kurtosis of the respiratory rate, $kurt(FFT_t^s(f))$, measured by ARCA 100, to the kurtosis of a pure spectrum of the respiratory rate, $kurt(p_{rr_t^s})$, comprising only the estimated breathing frequencies of the user. The greater the value of $q_t^s$ (greater than one), the lower the quality of the estimated biomarker (e.g., respiratory rate) extracted by biomarker extractor 106 based on the signals. Again, a predetermined threshold can be set to determine whether ARCA 100 accepts or rejects an estimate of a biomarker based on the quality metric $q_t^s$.

ARCA 100, in certain embodiments, can respond to a quality-based rejection of biomarker by determining a likely cause of the rejection. For example, ARCA 100 can determine whether the rejection is likely caused by the user incorrectly positioning the portable device used to capture signals from which the biomarker as extracted or whether the rejection is more likely caused by a failure of a component of the portable device. For example, as described above, ARCA 100 in some embodiments uses two separate methods to measure the same biomarker. For example, ARCA can measure respiratory rate or breathing frequency by (1) applying Fourier transformation and (2) determining a signal-to-noise ratio. An acceptable quality measure is likely if both techniques select the same preferred axis of measurement and extract biomarkers that quantitatively yield the same number or ones close to each other and that are within a normal or expected respiratory range. It is likely then there is no measurement or compliance failure. If, however, the measurements are not close and one is within a normal range of human breathing frequency and, for example, the user's heart rate is not elevated, there is a likelihood that the out of range estimate is due to a measurement failure. If both measurements are out of range, but the signal-to-noise ratio is low, then the problem may be either measurement failure or the user's failure to properly effect measurement using the portable device.

Accordingly, in instances in which measurement quality determiner 108 determines a measurement quality indicating either a measurement or compliance failure, ARCA 100 can consider related biomarkers (e.g., whether a user's heart rate is elevated) and/or other factors such as signal-to-noise ratio of selected signals. In certain embodiments, ARCA 100 can generate a feature vector whose elements include various biomarkers and/or other factors (e.g., operating data of the portable device, signal-to-noise ratio). The feature vector can be input into a machine learning model trained using sample data collected over time from multiple portable devices in which an ARCA operates. The machine learning model can be trained to distinguish between sensor (or measurement) failure and user compliance failure based on the feature vector input. In case of compliance failure, ARCA 100 can provide the user with an instruction on how to effect one or more re-measurements and for a sensor failure the system can recalibrate the algorithmic measurement performed to accurately estimate the biomarker. ARCA 100 can instruct a user to obtain a new measurement with the portable device and, if the new measurement is obtained successfully, the algorithm which estimates the biomarker can recalibrate itself to correspond more closely to specific physical characteristics of the user.

In embodiments in which ARCA 100 extracts biomarkers from signals captured simultaneously with different devices, selected signals may be misaligned (e.g., owing to drift of the respective devices' clocks). Any such misalignment can seriously erode the quality of biomarkers extracted from selected signals. Accordingly, ARCA 100 optionally includes signal synchronizer 110 for performing time-based aligning of signals simultaneously captured by separate devices. Illustratively, signal synchronizer 110 is implemented in software that executes on processor 112 for aligning signals captured by each device communicatively coupled to the portable device in which processor 112 is embedded. In other embodiments, signal synchronizer is implemented in dedicated circuitry or a combination of circuitry and software.

Signal synchronizer 110 initially pre-processes signals captured by separate devices. In pre-processing the captured signals, signal synchronizer 110 determines a sample rate for each such signal, ensuring that the signals are sufficient for generating an adequate amount of processing data. Pre-processing further includes adjusting any time shifts detected by signal synchronizer 110. Signal synchronizer 110 can adjust a time shift as follows. In response to detecting drift in clocked times between a pair of devices, signal synchronizer 110 identifies one device as the accurate timekeeper and marks the start and end times of a breathing task (e.g., tidal breathing during a one-minute interval) that generates sensor-detected signals recorded by the identified device. The identified device can serve as a hub for data collecting and processor for multiple sensors. For example, a smartphone can serve as the hub for data collecting and processor for both smartphone sensors and smartwatch sensors. Signal synchronizer 110 determines the precise start and end times of a waveform generated by the second device in response to the same breathing task during the same time interval. Using a sliding window of the same duration (e.g., one minute) based on the waveform generated by the second device, signal synchronizer 110 iteratively advances the window in smaller time increments (e.g., 100 milliseconds) relative to the waveform generated by the first device. Starting in the temporal vicinity of the start time of the first device's waveform, signal synchronizer 110 advance the sliding window until a best or optimal match is found, thereby aligning the waveforms.

In some embodiments, signal synchronizer 110 determines the best or optimal match based on a cross-correlation (e.g., Pearson's r). Signal synchronizer 110 determines the cross-correlation between the waveform generated by the first device and the waveform generated by the second device at each of the smaller time increments (e.g., 100 milliseconds) during the advancing of the window. The best match is determined by the cross-correlation. For example, using Pearson's r, signal synchronizer determines a closeness or similarity between the waveforms based on n samples of the two waveforms:

$$r_{xy} = \frac{\sum_{i=1}^{n}(x_i - \bar{x})(y_i - \bar{y})}{\sqrt{\sum_{i=1}^{n}(x_i - \bar{x})^2}\sqrt{\sum_{i=1}^{n}(y_i - \bar{y})^2}}$$

where $x_i$ is the i-th sample of the waveform generated by signals captured by the first device and $y_j$ is the i-th sample of the waveform generated by signals captured by the second device. The closer that $r_{xy}$ is to one the closer the match between the two waveforms. Signal synchronizer 110 concludes pre-processing by normalizing the respective devices' signals over the predetermined time duration (e.g., one minute).

In an example implementation, signal synchronizer 110 performs signal processing on the signals using a third-order Savitzky-Golay filter and determines a maximum frequency component after determining a Kurtosis-based quality indicator, $q_r$, as described above. One advantage of the Savitzky-Golay filter's polynomial smoothing already noted is the smoothing coupled with preservation of signal peaks. Signal synchronizer 110 determines the expected peak-to-peak distance of the waveform and identifies relevant peaks by allowing peak-to-peak distances D greater than or equal to $c_i*D_{ep}$ (e.g., $c_1=0.75$), where $D_{ep}$ is an expected duration or time-based distance (empirically determined). Signal synchronizer 110 discards any spurious peak, which, as defined above, is one whose height is less than a tenth percentile of the median peak height and which is too close to another peak (e.g., less than or equal to 20 percent of a determined breath duration, λ). Signal synchronizer 110 generates two time series, each comprising peak timestamps for signals generated by a different device (e.g., a smartwatch-captured abdominal signal and a smartphone-captured thoracic signal for determining respiratory synchrony). The breath duration, λ, is estimated by signal synchronizer 110 based on a combination (e.g., median) of peak timestamps related to the different signals (e.g., abdominal and thoracic signals). For a minimum number of peak timestamps between end and start of the waveform used as the reference, signal synchronizer 110 determines the closest peak pairs ($T_i$, $T_1$) from the other timeseries and computes the phase difference, $\theta = 360/\lambda*|T_i-T_j|$, of each pair. In the context of respiratory synchrony using thoracic and abdominal signals, for example, the median θ is the thoracic-abdominal synchrony biomarker.

The alignment of the waveforms eliminates machine-induced misalignment (e.g., drift of the respective devices' clocks). The alignment provides signals from which biomarkers can be extracted with high confidence of reliability. Differences that remain are thus sure not to be induced by machine-based misalignment. Rather, differences can indicate an underlying lung condition. For example, thoraco-abdominal asynchrony, an indicator of various types of respiratory disorders and/or respiratory muscle dysfunctions, can be identified based on measuring thoracic signals with a first device and abdominal breathing with a second device. Different devices can be used. For example, the first device can be a smartphone and the second device a smartwatch, or the first can be a smartwatch and the second a smartphone. Irrespective of the which specific devices are used, the alignment procedure compensates for clock drift while preserving any phase difference. Once the respective signals are properly aligned (e.g., to remove drift), a phase difference clearly reveals an actual, non-machine difference. The phase difference provides clear evidence of thoraco-abdominal asynchrony.

In still other embodiments, ARCA 100 can be implemented in portable devices that enable the extraction of biomarkers from signals captured in passive mode, rather than requiring explicit action by the user. In certain embodiments, ARCA 100 is implemented in a pair of earbuds communicatively coupled, for example, to a smartphone. In other embodiments, ARCA 100 can be implemented using a neckband with an embedded microphone. These and other devices, many of which can be comfortably worn, can passively capture various signals from which biomarkers can be extracted. The signals can include acoustic signals, capacitive signals, and/or signals generated by motion sensors in response a user's body movements, as described above. As already described, ARCA 100 in simultaneously capturing signals using a combination of different devices can synchronize the selected signals to ensure extraction of reliable biomarkers.

Signal filter 104 can be configured to filter capacitive signals using, for example, a fourth-order Butterworth band-pass filter, with $f_{Low}=0.3$ Hz and $f_{High}=2$ Hz, a frequency range that reflects the natural variation of adult breathing frequencies. Signal filter 104 can apply to captured capacitive signals a hill-climbing peak detection algorithm with thresholds for determining positive and negative slope set to σ/2, where σ corresponds to standard deviation of the captured signal. In setting thresholds automatically, signal filter 104 identifies a capture duration for which there is a high probability that the duration captures several of a user's respiratory cycles.

A portable device whose form factor allows the device to be placed on or around the user's throat and/or ear can capture acoustic signals. Notably, such device can passively capture acoustic signals, thereby obviating a need for purposive effort by the user. Earbuds or headphones, for example, can provide passive breathing monitoring. Earbuds or headphones can capture breathing sounds when positioned to capture the sounds of airflow corresponding to a user's breathing. The user's ear, nose, and throat (ENT) channels are connected channels for airflow corresponding to the user's breathing. Earbuds or headphones can capture sounds and corresponding motion to identify whether current sounds are breathing sounds and, if so, can extract the breathing parameters.

Biomarkers, in certain embodiments, are extracted using a combination of signal processing and machine learning techniques. Three domain features each of a set of training samples for machine-learning classification are time, frequency, and cepstral. The frequency spectrum of signals generated with acoustic detection of a user's breathing is different from other sounds, such as coughing, wheezing, speaking, eating, and drinking. Time domain features of such signals include zero crossing rate (ZCR), spectral features include spectral power, sub-band power, spectral roll-off, spectral flux, and cepstral coefficient (including Mel-frequency cepstral coefficients (MFCCs)). MFCCs can be extracted using the discrete cosine transform of log-scaled outputs of FFT coefficients filtered by a triangular band-pass filter bank. In one embodiment, signal filter 104 uses 20 filters and calculates the first 12 coefficients, which ARCA 100 (e.g., collectively with other adaptive respiratory condition assessors) can provide for training the machine learning model to detect breathing segments in determining a respiratory condition.

In one embodiment, ARCA 100 is implemented in earbuds. An IMU of one or more of the earbuds captures motion-generated signals. Measurement axis selector 102 can select a preferred axis of measurement, as described above. Signal filter 104 can process the captured signals as follows. Signal filter 104 can eliminate signal sifts and trends by subtracting from each axis, channel, and/or dimension a moving average window of a predetermined number of samples (e.g., 3 samples). Signal filter 104 can additionally apply an averaging filter with a different window size (e.g. 2 samples) to each component, corresponding to one respiration cycle at a predetermined breathing rate (e.g. 30 BPM). Signal filter 104 can apply a cubic spline interpolation and resample the resulting signal at 256 Hz (as there typically are small variations in timestamps due, for example, to Bluetooth latency) in creating equidistant samples. Signal filter 104 discards windows exhibiting too great a movement. For example, if three percent or more of all accelerometer data points are above a predetermined threshold (e.g., 10 m/s$^2$), the entire sequence is discarded. Signal filter 104 can apply hard thresholding, retaining only samples within ±2 standard deviations (SD). Signal filter 104 can use a fourth-order bandpass Butterworth filter with cut-off frequencies of 0.1 Hz and 0.5 Hz, which substantially de-noises signals and approximately corresponds to a human respiratory rate of 6 to 30 BPM. To further smooth captured signals while retaining the peak positions, signal filter 104 can use a triangle filter with a width of 2 seconds. To make the results independent of changes on different axes for different postures of the user's body, signal filter 104 can perform a principal component analysis (PCA). Signal filter 104 can perform a spectral analysis of each principal component using a Fast Fourier Transformation (FFT) with zero-padding and compute the maximum peak and its magnitude for each component. Signal filter 104 identifies the frequency corresponding to the peak with the highest magnitude as a respiration frequency converted to units of breaths per minute (BPM).

Operatively, with ARCA 100 implemented in a smartphone communicatively coupled to a pair of earbuds, the earbuds can capture signal data from both the left and right earbud using a Bluetooth connection to the smartphone. The left and right earbuds can generate two separate data streams with timestamps. The data can be captured from the earbuds' triaxial accelerometer, triaxial gyroscope, triaxial magnetometer, or any combination thereof. Optionally, in one embodiment, ARCA 100 can determine whether the user is wearing the earbuds based on detecting one or more physiological conditions of the user, such as heart rate, breathing rate or other such condition or combination of conditions, separately from left and right earbuds. In yet another embodiment, ARCA 100 can determine the wearing status based on detecting head motions of the user captured by the IMU of each of the ear buds. If ARCA 100 detects that the devices are not being worn by the user, ARCA 100 can optionally notify the user of the detected status via the smartphone or even another device communicatively coupled with the earbuds.

When one earbud is worn and the other is not, ARCA 100 can extract biomarkers based on signals captured by the one earbud the user is wearing. When the user is wearing both earbuds, signal synchronizer 110 of ARCA 100 can synchronize the respiratory motion of the user's body captured by both earbuds. The sensor-generated signals separately captured by each earbud are likely to be infused with different levels of drift, as well as motion artifacts due to the difference in position and head motions. ARCA 100, according to one embodiment, can fuse the separate signals after removing the baseline drift via a windowed mean subtraction or the like. In another embodiment, ARCA 100 can fuse the separately captured signals through up-sampling or down-sampling for alignment. In yet another embodiment, ARCA 100 can compute a cross-correlation for corresponding respiratory cycles from each earbud and remove cycles that are highly affected by head motion of the user.

ARCA 100 can utilize the triaxial accelerometer, trial gyroscope, triaxial magnetometer, or their combinations for generating 6-axis or 9-axis motion sensor data streams. Due to positioning of the devices and any rotational head movement, one earbud channel may capture better respiratory movement and the other may capture better head motion. In one embodiment, ARCA 100 can determine the best channel based on the captured respiratory movements and discard the head motion. Once the best channel is determined, ARCA 100 according to one embodiment can use a time-based algorithm (e.g., zero crossing rate) or frequency-based algorithm (e.g., Fourier transformation) to estimate the biomarkers. In another embodiment, ARCA 100 can transform the best channel signal using principal component analysis (PCA) and then estimate biomarkers such as fractional inspiratory time, breathing rate, inhalation-exhalation ratio. In still another embodiment, ARCA 100 can distinguish the respiratory movements due to chest breathing from those due to abdominal breathing and, implemented with separate sensing devices (e.g., smartphone and smartwatch), determine whether there is a frequent alternation between the two types of breathing.

ARCA 100 can determine the quality of extracted biomarkers based on the agreement between the algorithmically determined estimates and whether the biomarker range is within a plausible range (e.g., 8 to 30 BPM). If the quality of a respiratory rate is not acceptable, ARCA 100 according to one embodiment can discard the biomarkers from a current assessment window. In one embodiment, ARCA 100 retains only the biomarkers identified as having acceptable quality or reliability. The retained biomarkers can be used as features of training samples for various machine learning algorithms for training one or more classification models for classifying the respiratory health and/or wellness status of a user based on one or more current biomarkers. Moreover, the machine learning can be used for distinguishing healthy individuals from ones who may be infected with a respiratory disease or otherwise afflicted with a respiratory condition. In another embodiment, a model constructed with machine learning can be used to classify an individual according to different breathing patterns, including ones identified by the model as corresponding to out-of-norm or unhealthy individuals.

ARCA 100 in other embodiments is implemented in a portable device having a receiver-transmitter array. Using the receiver-transmitter array to capture sensor signals generated in response to body movements due to lung activity, ARCA 100 can use signals generated in response to movements of different regions of the user's body. ARCA 100 can use beam forming to acquire signals from movements, for example, in the thoracic region and the abdominal region.

Using beam forming, ARCA 100 can determine a direction of arrival of signals that are transmitted by a transmitter of the receiver-transmitter array and reflected by the user's body back to a receiver of the receiver-transmitter array. ARCA 100 can separately identify chest displacements and abdominal displacements of the user's body during one or more respiratory cycles based on the signals reflected from the user's body and received by the receiver of the receiver-transmitter array. Optionally, ARCA 100 can convey one or more electronic messages to the user from the portable device, the one or more messages instructing the user to re-orient the portable device relative to the user's body to calibrate additional signals subsequently transmitted and reflected back to the receiver. In some embodiments, ARCA 100 determines the user's respiratory condition based on a thoraco-abdominal synchrony determined using a chest breathing rate biomarker estimated by the chest displacements and an abdominal breathing rate biomarker estimated by the abdominal displacements.

FIG. 4 is a flowchart of example method 400 of adaptively assessing a human respiratory condition, according to an embodiment. Method 400 can be performed by a system the same or similar to the ones described with reference to FIGS. 1-3. The system at block 402 captures, with a portable device, a plurality of signals generated by one or more sensors of the portable device as the portable device is positioned to sense a portion of a human user's body. The one or more sensors generate the plurality of signals in response to sensor-detected movements of the user's body measured along multiple axes, the movements corresponding to lung activity of the user's body during one or more respiratory cycles.

At block 404, the system selects, using signal processing performed by a signal processor embedded in the portable device, a preferred axis of measurement from among the multiple axes. The system at block 406 filters, with the signal processor, waveforms generated by selected signals selected from among the plurality of signals, the selected signals corresponding to signals generated in response to movements of the user's body measured along the preferred axis of measurement.

At block 408, the system extracts from the waveforms, using the signal processor, one or more biomarkers corresponding to the lung activity. Based on the one or more respiratory biomarkers, the system determines a respiratory condition of the user at block 410. The system at block 412 generates a notification based on the determined respiratory condition and at block 414 conveys the notification to the user via the portable device. For example, a text message or other visual indicator can be presented to the user on a screen display of the portable device, the message informing the user of the determined respiratory condition (e.g., healthy, unhealthy). Optionally, the text message, as appropriate, can described any follow-up action recommended to the user (e.g., consult a physician). Instead, or additionally, for example, an audio message can be provided via a portable device speaker informing the user of the determined respiratory condition and, optionally, any recommended follow-up action. In certain embodiments, if one or more biomarkers indicates a healthy respiratory condition, the system can suggest (via text or audible message) that the user confirm the result with a rigorous confirmatory test, such as spirometry performed with the portable device, but if the biomarker(s) indicate an unhealthy respiratory condition, the system can suggest a less rigorous test (e.g., A-vowel test) commensurate with the determined lung condition. The less rigorous test (e.g., A-vowel test) also can be one performed with the portable device.

In some embodiments the system estimates a measurement quality of the signals captured by the portable device, the measurement quality indicating a likelihood that the signals as captured reliably detect the movements corresponding to the lung activity during the one or more respiratory cycles. The system can further determine based on the measurement quality, one or more positions for the user to position the portable device relative to the user's body and generate an electronic message with the portable device based on the measurement quality. The electronic message can instruct the user to position the portable device relative to the user's body, in accordance with the one or more positions determined, for capturing a new plurality of signals generated by the one or more sensors of the portable device in response to further sensor-detected movements of the user's body during one or more new respiratory cycles.

In some embodiments, the system can determine the one or more positions by selecting from a plurality of breathing tests a breathing test for the user to perform with the portable device, the breathing test selected based on a likelihood that meets or exceeds a predetermined probability level that, given the determined respiratory condition of the user, the user is capable of performing the breathing test. The system can determine the one or more positions based on the breathing test selected for the user to perform.

The system can determine based on the initially determined lung condition an additional test, either in confirmation of the initial determination or as an adjunct to the determination to diagnose a possible adverse lung condition.

The system can determine lung condition using a machine learning or statistical model stored by the system or accessible to the system via a network connection. A machine learning model can be trained to classify the user's lung condition based on biomarkers extracted by the system and input into the model in a data structure, such as a feature vector, generated by the system. The model can be trained using sample data (biomarkers) collected from multiple subjects tested under clinical conditions. The model can be trained using machine learning to classify based on input in the form of feature vectors whose elements are extracted biomarkers. The model can identify a condition and classify the condition as mild, moderate, or severe, for example. In various embodiments, the system can use different machine learning models such as a multi-layer deep learning model, Support Vector Machine (SVM), random forest, or logistic regression, for example. The machine learning model can be trained using training data comprising breathing frequency, fractional inspiratory time, and/or I:E ratio, for example, as well as other biomarkers, such as heart rate, heart rate variability, oxygen saturation (SpO2). In other embodiments, the model can be a statistical model, such as linear or non-linear multiple regression.

Based on a determined lung condition, the system can determine a test for the user to perform with a portable device. The system can determine that given a particular lung condition, the user should perform a particular test. For example, the system can suggest that the user, given a lung condition determination, perform a less stressful test such as the A-vowel test using the portable device. The system can generate, as described above, a text or audible message conveyed to the user with the portable device instructions on the proper way to perform self-testing with the portable device.

In other embodiments, the system uses multiple portable devices. Multiple time-based waveforms, each waveform generated based on sensor-detected signals, are captured by a different one of the portable devices, with each of the portable device positioned to capture a set of signals generated in response to sensor-detected movements of a different portion of the user's body during the one or more respiratory cycles. The system determines, based on a timestamp automatically generated by a selected one of the multiple portable devices, a baseline start time for the plurality of time-based waveforms, the baseline start time corresponding to the one or more respiratory cycles. The system time-aligns each of the time-based waveforms based on the baseline start time.

In one embodiment, the multiple portable devices comprise a first portable device and a second portable device. The first portable device is positioned adjacent a chest portion of the user's body. The second portable device position adjacent an abdominal portion of the user's body. The first portable device generates a first time-based waveform by capturing and signal processing a plurality of signals generated in response to sensor-detected movements of the chest portion of the user's body during the one or more respiratory cycles. The second portable device generates a second time-based waveform by capturing and signal processing a plurality of signals generated in response to sensor-detected movements of the abdominal portion of the user's body during the one or more respiratory cycles. The system estimates a breathing synchrony of the user based on a phase difference between the first and second time-based waveforms and determines the respiratory condition of the user based on the estimated breathing synchrony.

In still other embodiments, the system uses a portable device in which is embedded a receiver-transmitter array. Using beam forming, the system determines a direction of arrival of signals transmitted by a transmitter of the receiver-transmitter array and reflected by the user's body back to a receiver of the receiver-transmitter array. The system separately identifies chest displacements and abdominal displacements of the user's body during the one or more respiratory cycles. The system can optionally convey one or more electronic messages to the user from the portable device, the one or more messages instructing the user to re-orient the portable device relative to the user's body to calibrate additional signals subsequently transmitted and reflected back to the receiver. The system can determine the respiratory condition of the user's body based on a thoraco-abdominal synchrony determined using a chest breathing rate biomarker estimated by the chest displacements and an abdominal breathing rate biomarker estimated by the abdominal displacements. In some embodiments, the plurality of signals comprises acoustic signals, and the portable device comprises an electroacoustic transducer worn by the user (e.g., earbuds, microphone-embedded neckband). The electroacoustic transducer is configured to capture acoustic signals generated by the user when breathing, speaking, or coughing.

Figure 5:
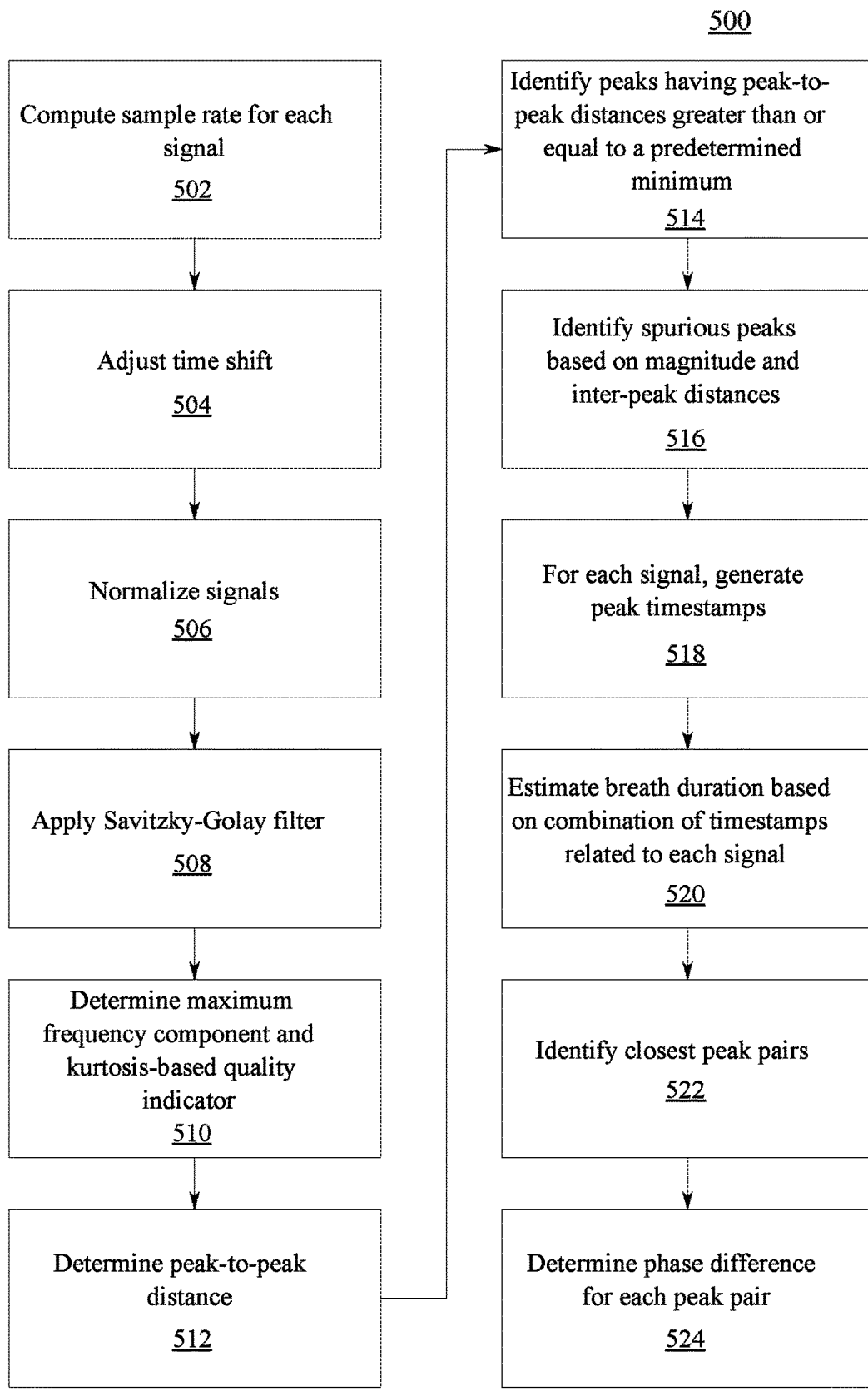
FIG. 5 is a flowchart of an example method for synchronizing waveforms generated by signals captured simultaneously by separate devices as part of an adaptive assessment of a human respiratory condition in accordance with one or more embodiments described herein.

FIG. 5 is a flowchart of example method 500 for synchronizing waveforms generated by signals captured simultaneously by separate devices as part of adaptively assessing a human respiratory condition, according to an embodiment. Method 500 can be performed by a system the same or similar to the ones described with reference to FIGS. 1-3. The system at block 502 computes a sample rate for each signal captured by a separate device. At block 504, the system adjusts the waveforms for any time shift misalignment (e.g., clock draft) of the respective signals captured by separate devices. The system at block 506 normalizes each of the respective signals captured by separate devices.

At block 508, the system filters the signals. For example, to effect signal smoothing while preserving the sharpness of signal peaks the system can filter the signals by applying a Savitzky-Golay filter. The system at block 510 determines the maximum frequency component. The maximum frequency component can be determined after determining a measure quality indicator. The measure quality indicator can be a kurtosis-based quality indicator, which provides an indication of signal "purity" measured as a ratio of the noise-infused signal as captured relative to the noise free signal with the same periodicity. The kurtosis-based quality indicatory can be generated by the system using the frequency component-based procedure, as described above. The system at block 512 determines peak-to-peak distances, that is, the time between successive waveform maxima.

At block 514, the system identifies peaks having peak-to-peak distances (time differences) greater than or equal to a predetermined minimum (e.g., expected breath duration). The system identifies spurious peaks at block 516, the identification based on the amplitude magnitudes and distances between each peak pair.

At block 518, the system generates timestamps corresponding to each peak of each signal. The system at block 520 estimates breath duration based on a combination (e.g., the median) of the timestamps related to each signal. The system at block 522 identifies the closest pair of peaks. At block 524 the system determines the phase difference for each peak pair.

In the specific context of determining breathing synchrony based on biomarkers extracted from signals generated by a first device and a second device, the system at block 524 can determine a phase difference for each peak pair.

Figure 6:
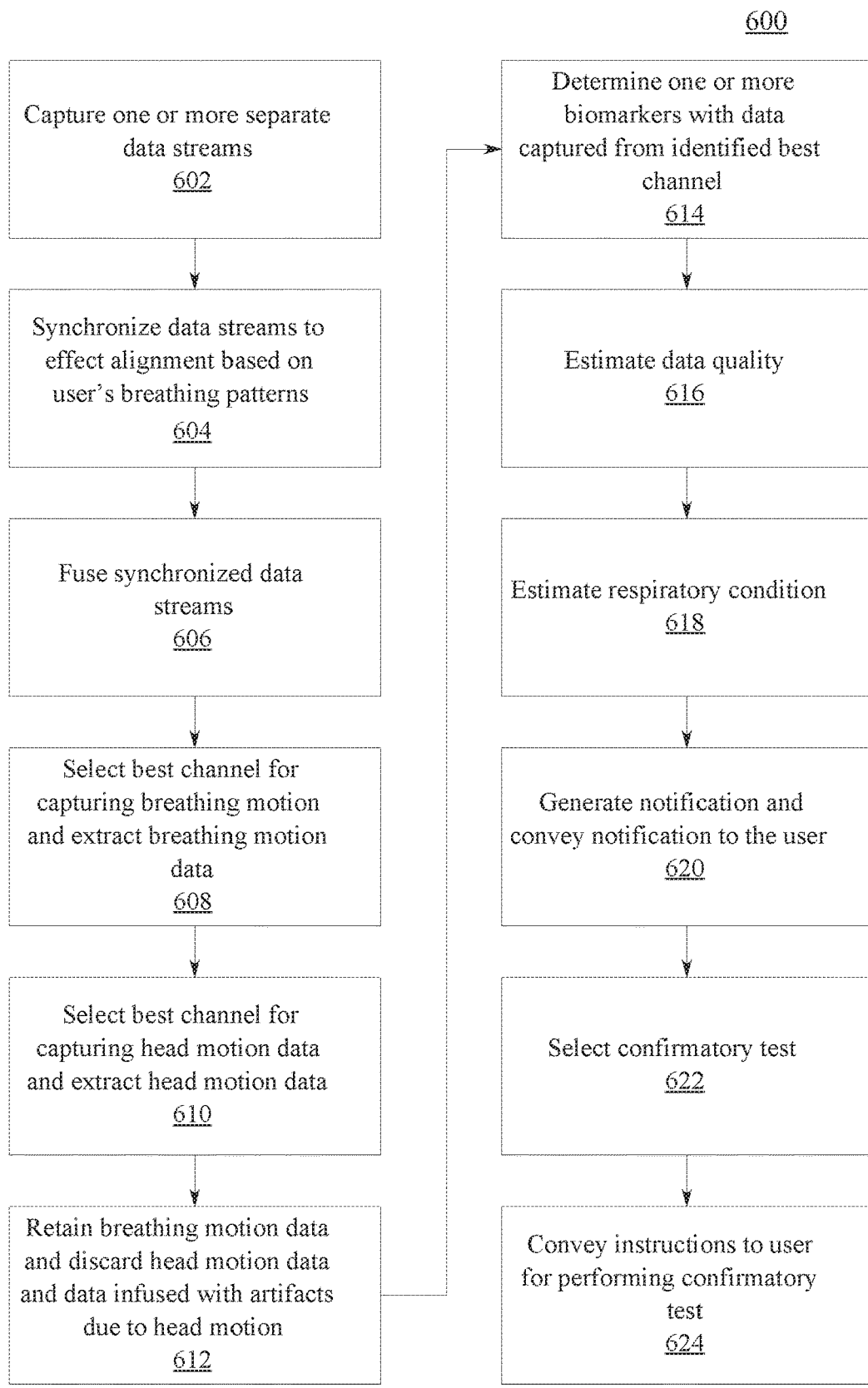
FIG. 6 is a flowchart of an example method of simultaneously capturing separate signals for adaptively assessing a human respiratory condition in accordance with one or more embodiments described herein.

FIG. 6 is a flowchart of example method 600 of extracting biomarkers from signals captured using one or more passive-sensing devices. Method 600 can be performed by a system the same or similar to the systems described with reference to FIGS. 1-3 for capturing acoustic, capacitive, and/or motion-induced signals. Illustratively, method 600 is implemented in a system comprising two earbuds worn by a user and communicatively coupled (e.g., via Bluetooth or wired connection) with a smartphone carried by the user. The communicatively coupled earbuds and smartphone can passively monitor a user's breathing, as well as sounds such as coughing.

At block 602, a left and a right earbud each generates separate data streams which are captured by the system. The data streams generated can include timestamps indicating the times in which underlying signals from which the data are extracted are captured by a triaxial accelerometer, triaxial gyroscope, and/or triaxial magnetometer embedded in each of the earbuds.

At block 604 the data streams are synchronized. The data streams can comprise data corresponding to breathing patterns of the user. The system can synchronize the data streams to coincide with the user's breathing pattern. Baseline drift and motion artifacts due to head motions of the user and the separate placement of the earbuds, in some embodiments, are removed by a windowed-mean subtraction of each data sample. In some embodiments, the system aligns the data streams using up-sampling or, in other embodiments, down-sampling the data. In still other embodiments, the separate data streams are aligned using a sliding window to determine an optimum match based on a cross-correlation corresponding the breathing cycles captured by each earbud. Breathing cycles that are highly affected by head motions unrelated to the users breathing are removed. The aligned data samples are fused at block 606.

Due to the separate positioning of each bud and head movements of the user, one channel may capture better the user's breathing motion and the other channel may capture better the user's head motions. Accordingly, in some embodiments, the system at block 608 determines based on IMU data captured by each earbud the best channel (corresponding to the left or right earbud) for capturing motions corresponding to the user's breathing. The system extracts breathing motion data from the identified best channel.

Having determined the best channel for capturing data corresponding to the user's breathing, the system at block 610 identifies the alternative channel for capturing head motion data and extract head motion data. At block 612, the system retains the best captured data corresponding to the user's breathing and discards data corresponding to the user's head motions and data infused with artifacts dues to head motion.

The advantage of obtaining data corresponding to the user breathing from an identified best channel and obtaining head motion data from the other is available only if the user is wearing both earbuds. Accordingly, the system optionally can determine the wearing status of the earbuds and, in the event the user is wearing only one can provide the user an advisement (e.g., via the communicatively coupled smartphone) suggesting the user wear both for a better lung condition assessment. The system, in certain embodiments, determines the wearing status of the earbuds based on one or more biomarkers (e.g., heart rate, breathing rate, combination thereof) extracted separately from the from left and right earbuds. That is, only the worn earbud provides the biomarker in the event the user is wearing only one. In other embodiments, the system determines the wearing status based on whether head motions are captured by each of the earbuds or only one currently worn by the user.

At block 614, once a best channel is determined, the system determines one or more biomarkers. In various embodiments, the system determines a biomarker using a time-based algorithm (e.g., zero crossing rate), frequency-based algorithm (e.g., Fourier transformation), or other procedure described above for estimating biomarkers. The system optionally can transform the best channel signal using principal component analysis (PCA) and then estimate breathing biomarkers such as fractional inspiratory time, breathing rate, inhalation-exhalation ratio. In one embodiment, the system distinguishes the breathing motion due to chest breathing and the belly breathing and determines whether there is a frequent alternation between the two types of breathing. In some embodiments, abdominal breathing sounds and motion different from the thoracic (chest) breathing sounds and motion are captured by earbuds alone. In other embodiments, possibly more accurate measurements are obtained using the earbuds in conjunction with a smartphone or smartwatch positioned against the user's abdomen to capture signals generated in response to abdominal breathing.

At block 616, the system estimates the quality of the data that provide the basis of the estimates of one or more biomarkers and whether the biomarkers are plausible (e.g., whether a breathing rate is within 8 to 30 BPM). The system can determine quality based on a quality metric generated by the agreement-based procedure and/or the frequency component-based procedure. If the system determines that the quality is unacceptable or a biomarker is implausible (based on clinically determined data), then optionally the system can generate an instruction (e.g., conveyed via the smartphone) instructing the user to actively perform a procedure to generate new data (e.g., using the smartphone) from which a reliable biomarker can be extracted.

At block 618, based on one or more initial or subsequently estimated biomarkers, the system estimates the user's respiratory condition. In some embodiments, the system can generate a feature vector whose elements comprise one or more of the estimated biomarkers. The system can input the feature vector into a model trained using machine learning, the model stored for example in memory of the smartphone or accessible to the smartphone via a network connection. Based on the feature vector, the model can classify the user's lung condition as healthy or unhealthy, for example. Depending on the type of machine learning model (e.g., multi-classification model) and the nature of the data (e.g., clinical data) used to train the model, the system in some embodiments determines based on estimated biomarkers whether the user's lung condition is healthy or not and, if unhealthy, the likely cause and/or severity of the unhealthy condition.

At block 620, the system generates a notification notifying the user of the user's estimated respiratory condition and conveys the notification to the user (e.g., via a user interface of the smartphone). At block 622, the system optionally selects a confirmatory test for the user to perform based on the estimated respiratory condition of the user. For example, an estimated respiratory condition can dictate that the user should perform a non-strenuous breathing test (e.g., long vowel test). At block 624, the system can convey instruction (again, e.g., via a user interface of the smartphone) instructing the user of a proper procedure for performing the test (e.g., speaking a long vowel into the smartphone microphone).

In some embodiments, the system includes a microphone (embedded in an earbud or in the smartphone) that passively monitors for sounds such as a cough emanating from the user. The system can be trained (e.g., using a machine learning model) to recognize certain sounds having predetermined characteristics. The system responds to recognition of such sounds by conveying instructions (e.g., via the smartphone interface) to the user to perform one or more breathing tests to invoke ARCA processing to determine the user's lung condition and whether the user's lung condition is healthy or not.

FIG. 7 illustrates an example portable device 700 in accordance with one or more embodiments described within this disclosure. Portable device 700 can include a memory 702, one or more processors 704 (e.g., image processors, digital signal processors, data processors), and interface circuitry 706.

In one aspect, memory 702, processor(s) 704, and/or interface circuitry 706 are implemented as separate components. In another aspect, memory 702, processor(s) 704, and/or interface circuitry 706 are integrated in one or more integrated circuits. The various components of portable device 700 can be coupled, for example, by one or more communication buses or signal lines (e.g., interconnects and/or wires). In one aspect, memory 702 may be coupled to interface circuitry 706 via a memory interface (not shown).

Sensors, devices, subsystems, and/or input/output (I/O) devices can be coupled to interface circuitry 706 to facilitate the functions and/or operations described herein, including the generation of sensor data. The various sensors, devices, subsystems, and/or I/O devices may be coupled to interface circuitry 706 directly or through one or more intervening I/O controllers (not shown).

For example, location sensor 710, light sensor 712, and proximity sensor 714 can be coupled to interface circuitry 706 to facilitate orientation, lighting, and proximity functions, respectively, of portable device 700. Location sensor 710 (e.g., a GPS receiver and/or processor) can be connected to interface circuitry 706 to provide geo-positioning sensor data. Gyroscope 716, magnetometer 718, and/or accelerometer 720 can be connected to interface circuitry 706 to provide sensor data based on detected movements corresponding to lung activity in a user's body during one or more respiratory cycles, as described herein. Altimeter 722 (e.g., an integrated circuit) can be connected to interface circuitry 706 to provide sensor data that can be used to determine altitude. Heart rate sensor 724 can be connected to interface circuitry 706 to generate sensor data and facilitate measurement of a heartbeat and the determination of a heart rate.

Camera subsystem 726 can be coupled to an optical sensor 728. Optical sensor 728 can be implemented using any of a variety of technologies. Examples of optical sensor 728 include a charged coupled device (CCD), a complementary metal-oxide semiconductor (CMOS) optical sensor, and the like. Camera subsystem 726 and optical sensor 728 can be used to facilitate camera functions, such as recording images and/or video clips (hereafter "image data"). In one aspect, image data is a subset of sensor data.

Communication functions can be facilitated through one or more wireless communication subsystems 730. Wireless communications subsystem(s) 730 can include radio frequency receivers and transmitters, optical (e.g., infrared) receivers and transmitters, and so forth. The specific design and implementation of wireless communication subsystem(s) 730 can depend on the specific type of portable device 700 implemented and/or the communication network(s) over which portable device 700 is intended to operate.

For purposes of illustration, wireless communication subsystem(s) 730 may be designed to operate over one or more mobile networks (e.g., GSM, GPRS, EDGE), a Wi-Fi network that may include a WiMax network, a short-range wireless network (e.g., a Bluetooth network), and/or any combination of the foregoing. Wireless communication subsystem(s) 730 can implement hosting protocols such that portable device 700 can be configured as a base station for other wireless devices.

Audio subsystem 732 can be coupled to a speaker 734 and a microphone 736 to facilitate voice-enabled functions, such as voice recognition, voice replication, digital recording, audio processing, and telephony functions. Audio subsystem 732 is able to generate audio type sensor data. In one or more embodiments, microphone 736 may be utilized as a respirator sensor.

I/O devices 738 can be coupled to interface circuitry 706. Examples of I/O devices 738 include, for example, display devices, touch-sensitive display devices, track pads, keyboards, pointing devices, communication ports (e.g., USB ports), network adapters, buttons or other physical controls, and so forth. A touch-sensitive device such as a display screen and/or a pad is configured to detect contact, movement, breaks in contact, and the like using any of a variety of touch sensitivity technologies. Example touch-sensitive technologies include, for example, capacitive, resistive, infrared, and surface acoustic wave technologies, other proximity sensor arrays or other elements for determining one or more points of contact with a touch-sensitive device, and the like. One or more of I/O devices 738 may be adapted to control functions of sensors, subsystems, and such of portable device 700.

Portable device 700 further includes a power source 740. Power source 740 able to provide electrical power to various elements of portable device 700. In one embodiment, power source 740 is implemented as one or more batteries. The batteries may be implemented using any of a variety of different battery technologies, whether disposable (e.g., replaceable) or rechargeable. In another embodiment, power source 740 is configured to obtain electrical power from an external source and provide power (e.g., DC power) to the elements of portable device 700. In the case of a rechargeable battery, power source 740 further may include circuitry that is able to charge the battery or batteries when coupled to an external power source.

Memory 702 can include random access memory (e.g., volatile memory) and/or non-volatile memory, such as one or more magnetic disk storage devices, one or more optical storage devices, flash memory, and so forth. Memory 702 can store operating system 752, such as LINUX, UNIX, a mobile operating system, an embedded operating system, and the like. Operating system 752 may include instructions for handling system services and for performing hardware-dependent tasks.

Memory 702 may store additional program code 754. Examples of other program code 754 may include instructions to facilitate communicating with one or more additional devices, one or more computers, and/or one or more servers; graphic user interface processing; processing instructions to facilitate sensor-related functions; phone-related functions; electronic messaging-related functions; Web browsing-related functions; media processing-related functions; GPS and navigation-related functions; security functions; camera-related functions, including Web camera and/or Web video functions; and so forth. Memory 702 may also store one or more other applications 762.

Memory 702 may store ARCA program code 756. ARCA program code 756 can be adapted to implement the various embodiments of an ARCA as described herein. Executing on one or more processors 704, ARCA program code 756 performs signal processing and other operations for estimating a user's respiratory condition based on biomarkers extracted from signals captured by portable device 700. In one or more embodiments, ARCA program code 756 facilitates the extraction of biomarkers from signals captured by portable device 700 (e.g., via a MEMS sensor, IMU, microphone 736 and/or other motion or sound transducers). The biomarkers correspond to one or more lung conditions and can be input to a machine learning classification model that may be incorporated into ACRA program code 756 or accessible to the ACRA via wireless communication subsystems 730 or a wired network connection of portable device 700. The ARCA program code 756, using the machine learning classification model, can generate one or more estimated lung conditions of a user based on the extracted biomarkers. The biomarkers correspond to lung functions and include respiratory (or breathing) rate, respiratory or breathing cycle, fractional inspiratory time, I:E ratio, FEV1, FVC, and FEV1/FVC ratio. The biomarkers can be used for the identification and determination of lung-related problems and treatment of various diseases. Further aspects of operations performed through execution of ARCA program code 756 are described herein with reference to the other figures.

Memory 702 may also store various types of data (not shown) such as sensor data, baseline data, data obtained by way of received user input(s), and/or data obtained by way of querying one or more external data sources.

The various types of instructions and/or program code described are provided for purposes of illustration and not limitation. The program code may be implemented as separate software programs, procedures, or modules. Memory 702 can include additional instructions or fewer instructions. Moreover, various functions of portable device 700 may be implemented in hardware and/or software, including in one or more signal processing and/or application-specific integrated circuits.

Program code stored within memory 702 and any data used, generated, and/or operated on by portable device 700 are functional data structures that impart functionality to a device when employed as part of the device. Further examples of functional data structures include, for example, sensor data, data obtained via user input, data obtained via querying external data sources, baseline information, and so forth. The term "data structure" refers to a physical implementation of a data model's organization of data within a physical memory. As such, a data structure is formed of specific electrical or magnetic structural elements within a memory. A data structure imposes physical organization on the data stored in the memory that is used by a processor.

In certain embodiments, one or more of the various sensors and/or subsystems described with reference to portable device 700 may be separate devices that are coupled or communicatively linked to portable device 700 through wired or wireless connections. For example, one or more (or all) of location sensor 710, light sensor 712, proximity sensor 714, gyroscope 716, magnetometer 718, accelerometer 720, altimeter 722, heart rate sensor 724, camera subsystem 726, audio subsystem 732, and so forth may be implemented as separate systems or subsystems that operatively couple to portable device 700 by way of I/O devices 738 and/or wireless communication subsystem(s) 730.

One or more of the sensors may be worn directly by the user and provide data to portable device 700 via a wired or wireless connection. Examples of additional sensors that are not illustrated in FIG. 7, but which may be used and/or worn by a user to provide sensor data to portable device 700 can include, for example, electrocardiography (ECG) sensors, photoplethysmography (PPG) sensors, gyroscopes, respiratory sensors, galvanic skin response (GSR) sensors, and the like. These additional sensors are represented in FIG. 7 by "other sensors" block 770. In one or more embodiments, sensors and/or subsystems as described herein are configured to generate sensor data that is stored in a memory external to portable device 700. Portable device 700 (e.g., processor(s) 704) may access externally stored sensor data for use and/or analysis as described herein.

Portable device 700 can include fewer components than those shown or include additional components other than those shown in FIG. 7 depending on the specific type of system that is implemented. Additionally, the particular operating system and/or application(s) and/or other program code included may also vary according to system type. Moreover, one or more of the illustrative components can be incorporated into, or otherwise form a portion of, another component. For example, a processor may include at least some memory.

Portable device 700 is provided for purposes of illustration and not limitation. A device and/or system configured to perform the operations described herein may have a different architecture than illustrated in FIG. 7. The architecture may be a simplified version of portable device 700 and may include a processor and memory storing instructions. The architecture may include one or more sensors as described herein. Portable device 700, or a similar system, can collect data using the various sensors of the device or sensors coupled thereto. It should be appreciated, however, that portable device 700 may include fewer sensors or other additional sensors.

Example implementations of portable device 700 include, for example, a smartphone or other mobile device or phone, a wearable computing device (e.g., smartwatch), a dedicated medical device or other suitable handheld, wearable, or comfortably carriable electronic device, capable of sensing and processing sensor-detected signals and data. It will be appreciated that embodiments can be deployed as a stand-alone device or deployed as multiple devices in a distributed client-server networked system. For example, in certain embodiments, a smartwatch can operatively couple to a mobile device (e.g., smartphone). The mobile device may or may not be configured to interact with a remote server and/or computer system.

The terminology used herein is only for the purpose of describing particular embodiments and is not intended to be limiting. Notwithstanding, several definitions that apply throughout this document are now presented.

As defined herein, the singular forms of terms "a," "an," and "the" are intended to include the plural forms as well, unless the context clearly indicates otherwise.

As defined herein, "another" means at least a second or more.

As defined herein, "at least one," "one or more," and "and/or," are open-ended expressions that are both conjunctive and disjunctive in operation unless explicitly stated otherwise. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B and C together.

As defined herein, "automatically" means without user intervention.

As defined herein, "computer readable storage medium" means a storage medium that contains or stores program code for use by or in connection with an instruction execution system, apparatus, or device. "Computer readable storage medium," as defined herein, is not a transitory, propagating signal per se. A computer readable storage medium may be, but is not limited to, an electronic storage device, a magnetic storage device, an optical storage device, an electromagnetic storage device, a semiconductor storage device, or any suitable combination of the foregoing. Memory elements, as described herein, are examples of a computer readable storage medium. A non-exhaustive list of more specific examples of a computer readable storage medium may include: a portable computer diskette, a hard disk, a random-access memory (RAM), a read-only memory (ROM), an erasable programmable read-only memory (EPROM or Flash memory), a static random-access memory (SRAM), a digital versatile disk (DVD), a memory stick, a floppy disk, or the like.

As defined herein, "includes," "including," "comprises," and/or "comprising," specify the presence of stated features, integers, steps, operations, elements, and/or components, but do not preclude the presence or addition of one or more other features, integers, steps, operations, elements, components, and/or groups thereof.

As defined herein, "if" means "when" or "upon" or "in response to" or "responsive to," depending upon the context. Thus, the phrase "if it is determined" or "if [a stated condition or event] is detected" may be construed to mean "upon determining" or "in response to determining" or "upon detecting [the stated condition or event]" or "in response to detecting [the stated condition or event]" or "responsive to detecting [the stated condition or event]" depending on the context.

As defined herein, "one embodiment," "an embodiment," "in one or more embodiments," "in particular embodiments," or similar language mean that a particular feature, structure, or characteristic described in connection with the embodiment is included in at least one embodiment described within this disclosure. Thus, appearances of the aforementioned phrases and/or similar language throughout this disclosure may, but do not necessarily, all refer to the same embodiment.

As defined herein, "output" means storing in physical memory elements, e.g., devices, writing to display or other peripheral output device, sending or transmitting to another system, exporting, or the like.

As defined herein, "processor" means at least one hardware circuit configured to carry out instructions contained in program code. The hardware circuit may be an integrated circuit. Examples of a processor include, but are not limited to, a central processing unit (CPU), an array processor, a vector processor, a digital signal processor (DSP), a field-programmable gate array (FPGA), a programmable logic array (PLA), an application-specific integrated circuitry (ASIC), programmable logic circuitry, and a controller.

As defined herein, "in response to" and "responsive to" mean responding or reacting readily to an action or event. Thus, if a second action is performed "in response to" or "responsive to" a first action, there is a causal relationship between an occurrence of the first action and an occurrence of the second action. The terms "in response to" and "responsive to" indicate the causal relationship.

As defined herein, "real time" means a level of processing responsiveness that a user or system senses as sufficiently immediate for a particular process or determination to be made, or that enables the processor to keep up with some external process.

As defined herein, "substantially" means that the recited characteristic, parameter, or value need not be achieved exactly, but that deviations or variations, including for example, tolerances, measurement error, measurement accuracy limitations, and other factors known to those of skill in the art, may occur in amounts that do not preclude the effect the characteristic was intended to provide.

As defined herein, the terms "user," "individual," and "subject" mean a human being.

The terms first, second, etc. may be used herein to describe various elements. These elements should not be limited by these terms, as these terms are only used to distinguish one element from another unless stated otherwise or the context clearly indicates otherwise.

Various embodiments of the inventive aspects disclosed herein may be implemented in a system, as a method, and/or in a computer program product at any possible technical detail level of integration. The computer program product may include a computer readable storage medium (or media) having computer readable program instructions thereon for causing a processor to carry out aspects of the embodiments disclosed herein. "Program code" is used interchangeably with "computer readable program instructions" within this disclosure. Computer readable program instructions described herein may be downloaded to respective computing/processing devices from a computer readable storage medium or to an external computer or external storage device via a network, such as the Internet, a LAN, a WAN, and/or a wireless network. The network may include copper transmission cables, optical transmission fibers, wireless transmissions, routers, firewalls, switches, gateway computers, and/or edge devices including edge servers. A network adapter cord or network interface in each computing/processing device receives computer readable program instructions from the network and forwards the computer readable program instructions for storage in a computer readable storage medium with the respective computing/processing device.

Computer readable program instructions for carrying out operations of the inventive arrangements disclosed herein may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language and/or procedural programming languages. The computer readable program instructions may execute entirely on a user's computer, partly on the user's computer, as a stand-alone software package, partly on the user's computer and partly on a remote computer or entirely on the remote computer or server. In the latter scenario, the remote computer may be connected to the user's computer through any type of network, including a LAN or a WAN, or the connection may be made to an external computer (for example, through the Internet using an Internet Service Provider). In some embodiments, electronic circuitry including, for example, programmable logic circuitry, an FPGA, or a PLA may execute the computer readable program instructions by utilizing state information of the computer readable program instructions to personalize the electronic circuitry, in order to perform aspects of the inventive arrangements described herein.

Certain aspects of the inventive arrangements are described herein with reference to flowchart illustrations and/or block diagrams of methods, apparatus (systems), and computer program products according to embodiments of the inventive arrangements. It will be understood that each block of the flowchart illustrations and/or block diagrams, and combinations of blocks in the flowchart illustrations and/or block diagrams, can be implemented by computer readable program instructions (e.g., program code).

These computer readable program instructions may be provided to a processor of a computer, special-purpose computer or other programmable data processing apparatus to produce a machine, such that the instructions, which execute via the processor of the computer or other programmable data processing apparatus, create means for implementing the functions/acts specified in the flowchart and/or block diagram block or blocks. Operatively coupling the processor to program code instructions transforms the machine of the processor into a special-purpose machine for carrying out the instructions of the program code. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the inventive arrangements described herein. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments provided herein have been presented for purposes of illustration and are not intended to be exhaustive or limited to the form and examples disclosed. The terminology used herein was chosen to explain the principles of the inventive arrangements, the practical application or technical improvement over technologies found in the marketplace, and/or to enable others of ordinary skill in the art understand the embodiments disclosed herein. Modifications and variations may be apparent to those of ordinary skill in the art without departing from the scope and spirit of the described inventive arrangements. Accordingly, reference should be made to the following claims, rather than the foregoing disclosure, as indicating the scope of such features and implementations.

What is claimed is:

1. A method, comprising:
   capturing, with a selected portable device, a plurality of signals generated by a plurality of sensors of a plurality of portable devices including the selected portable device, wherein the plurality of sensors are positioned to sense different portions of a human user's body, wherein the plurality of sensors generate the plurality of signals in response to sensor-detected movements of the different portions of the user's body measured along multiple axes, the movements corresponding to lung activity in the user's body during one or more respiratory cycles;
   selecting, using signal processing performed by a signal processor embedded in the portable device, a preferred axis of measurement from among the multiple axes;
   filtering, with the signal processor, waveforms generated by signals selected from among the plurality of signals, wherein the selected signals correspond to signals generated in response to movements of the different portions of the user's body measured along the preferred axis of measurement;
   within the selected portable device, time-aligning the waveforms corresponding to the plurality of portable devices and as filtered to adjust for drift of clocks of the respective plurality of portable devices, wherein the time-aligning is based on an iterative comparison of a window of the waveform of the selected portable device against the waveform of other ones of the plurality of portable devices;
   extracting from the waveforms, using the signal processor, a biomarker corresponding to each of the different portions of the user's body indicating the lung activity and, based on a breathing synchrony between the biomarkers of the different portions of the user's body, determining a respiratory condition of the user; and
   generating a notification based on the respiratory condition as determined.

2. The method of claim 1, further comprising estimating a measurement quality of the signals captured by the selected portable device, wherein the measurement quality indicates a likelihood that the signals as captured reliably detect the movements corresponding to the lung activity during the one or more respiratory cycles.

3. The method of claim 2, further comprising:
   based on the measurement quality, determining one or more positions for the user to position one or more of the plurality of portable devices relative to the user's body; and
   generating an electronic message by one or more of the plurality of portable devices instructing the user to position one or more of the plurality of portable devices relative to the user's body, in accordance with the one or more positions determined, for capturing a new plurality of signals generated by the one or more sensors in response to further sensor-detected movements of the user's body during one or more new respiratory cycles.

4. The method of claim 1, further comprising:
   selecting from a plurality of breathing tests a breathing test for the user to perform with the plurality of portable devices, wherein the breathing test is selected based on a likelihood that meets or exceeds a predetermined probability level that, given the determined respiratory condition of the user, the user is capable of performing the breathing test; and
   determining one or more positions for the user to position one or more of the plurality of portable devices relative to the user's body based on the breathing test selected for the user to perform.

5. The method of claim 1, wherein
   the plurality of portable devices comprises a first portable device and a second portable device, the first portable device positioned adjacent a chest portion of the user's body, and the second portable device position adjacent an abdominal portion of the user's body;
   the first portable device generates a first time-based waveform by capturing and signal processing a plurality of signals generated in response to sensor-detected movements of the chest portion of the user's body during the one or more respiratory cycles;
   the second portable device generates a second time-based waveform by capturing and signal processing a plurality of signals generated in response to sensor-detected movements of the abdominal portion of the user's body during the one or more respiratory cycles; and
   further comprising estimating the breathing synchrony based on a phase difference between the first and second time-based waveforms and determining the respiratory condition of the user based on the breathing synchrony.

6. The method of claim 1, wherein one or more of the plurality of portable devices has embedded therein a receiver-transmitter array, and wherein the method further comprises:
   using beam forming to determine a direction of arrival of signals transmitted by a transmitter of the receiver-transmitter array and reflected back by the user's body to a receiver of the receiver-transmitter array; and
   separately identifying chest displacements and abdominal displacements of the user's body during the one or more respiratory cycles, the separately identifying based on the signals reflected back from the user's body and received by the receiver of the receiver-transmitter array;
   wherein the determining the respiratory condition of the user's body is based on a thoraco-abdominal synchrony determined using a chest breathing rate biomarker estimated by the chest displacements and an abdominal breathing rate biomarker estimated by the abdominal displacements.

7. A system, comprising:
   a selected portable device including a processor, wherein the selected portable device is configured to perform:
   capturing a plurality of signals generated by a plurality of sensors of a plurality of devices including the selected portable device, wherein the plurality of sensors are positioned to sense different portions of a human user's body, wherein the plurality of sensors generate the plurality of signals in response to sensor-detected movements of the different portions of the user's body measured along multiple axes, the movements corresponding to lung activity in the user's body during one or more respiratory cycles;

selecting, using signal processing performed by a signal processor embedded in the selected portable device, a preferred axis of measurement from among the multiple axes;

filtering, with the signal processor, waveforms generated by signals selected from among the plurality of signals, wherein the selected signals correspond to signals generated in response to movements of the different portions of the user's body measured along the preferred axis of measurement;

time-aligning the waveforms corresponding to the plurality of portable devices and as filtered to adjust for drift of clocks of the respective plurality of portable devices, wherein the time-aligning is based on an iterative comparison of a window of the waveform of the selected portable device against the waveform of other ones of the plurality of portable devices;

extracting from the waveforms, using the signal processor, a biomarker corresponding to each of the different portions of the user's body indicating the lung activity and, based on a breathing synchrony between the biomarkers of the different portions of the user's body, determining a respiratory condition of the user; and generating a notification based on the respiratory condition as determined.

8. The system of claim 7, wherein the selected portable device is configured to further perform estimating a measurement quality of the signals captured by the selected portable device, wherein the measurement quality indicates a likelihood that the signals as captured reliably detect the movements corresponding to the lung activity during the one or more respiratory cycles.

9. The system of claim 8, wherein the selected portable device is configured to further perform:

based on the measurement quality, determining one or more positions for the user to position one or more of the plurality of portable devices relative to the user's body; and generating an electronic message by one or more of the plurality of portable devices instructing the user to position one or more of the plurality of portable devices relative to the user's body, in accordance with the one or more positions determined, for capturing a new plurality of signals generated by the one or more sensors in response to further sensor-detected movements of the user's body during one or more new respiratory cycles.

10. The system of claim 7, wherein the determining one or more positions comprises:

selecting from a plurality of breathing tests a breathing test for the user to perform with the plurality of portable devices, wherein the breathing test is selected based on a likelihood that meets or exceeds a predetermined probability level that, given the determined respiratory condition of the user, the user is capable of performing the breathing test; and determining one or more positions for the user to position one or more of the plurality of portable devices relative to the user's body based on the breathing test selected for the user to perform.

11. The system of claim 7, wherein
the plurality of portable devices comprises a first portable device and a second portable device, the first portable device positioned adjacent a chest portion of the user's body, and the second portable device position adjacent an abdominal portion of the user's body;

the first portable device generates a first time-based waveform by capturing a plurality of signals generated in response to sensor-detected movements of the chest portion of the user's body during the one or more respiratory cycles;

the second portable device generates a second time-based waveform by capturing a plurality of signals generated in response to sensor-detected movements of the abdominal portion of the user's body during the one or more respiratory cycles; and the processor is configured to initiate operations further including estimating the breathing synchrony based on a phase difference between the first and second time-based waveforms and determining the respiratory condition of the user based on the breathing synchrony.

12. The system of claim 7, further comprising:

a receiver-transmitter array configured to transmit signals and receive the transmitted signals reflected back from the user's body, wherein the selected portable device is further configured to perform:

using beam forming to determine a direction of arrival of the signals transmitted by a transmitter of the receiver-transmitter array and reflected back by the user's body to a receiver of the receiver-transmitter array; and separately identifying chest displacements and abdominal displacements of the user's body during the one or more respiratory cycles, the separately identifying based on the signals reflected back from the user's body and received by the receiver of the receiver-transmitter array;

wherein the determining the respiratory condition of the user's body is based on a thoraco-abdominal synchrony determined using a chest breathing rate biomarker estimated by the chest displacements and an abdominal breathing rate biomarker estimated by the abdominal displacements.

13. A computer program product comprising one or more computer readable storage media having program instructions collectively stored therein, the program instructions executable by a processor to cause the processor to initiate operations comprising:

capturing, with a selected portable device comprising the processor, a plurality of signals generated by a plurality of sensors of a plurality of portable devices including the selected portable device, wherein the plurality of sensors are positioned to sense different portions of a human user's body, wherein the one or more sensors generate the plurality of signals in response to sensor-detected movements of the different portions of the user's body measured along multiple axes, the movements corresponding to lung activity in the user's body during one or more respiratory cycles;

selecting a preferred axis of measurement from among the multiple axes;

filtering waveforms generated by signals selected from among the plurality of signals, wherein the selected signals correspond to signals generated in response to movements of the different portions of the user's body measured along the preferred axis of measurement;

time-aligning the waveforms corresponding to the plurality of portable devices and as filtered to adjust for drift of clocks of the respective plurality of portable devices, wherein the time-aligning is based on an iterative comparison of a window of the waveform of the selected portable device against the waveform of other ones of the plurality of portable devices;

extracting from the waveforms a biomarker corresponding to each of the different portions of the user's body indicating the lung activity and, based on a breathing synchrony between the biomarkers of the different portions of the user's body, determining a respiratory condition of the user; and generating a notification based on the respiratory condition as determined.

14. The computer program product of claim 13, the program instructions are executable by the processor to cause the processor to initiate operations further comprising estimating a measurement quality of the signals captured by the selected portable device, wherein the measurement quality indicates a likelihood that the signals as captured reliably detect the movements corresponding to the lung activity during the one or more respiratory cycles.

15. The computer program product of claim 14, the program instructions are executable by the processor to cause the processor to initiate operations further comprising:

based on the measurement quality, determining one or more positions for the user to position one or more of the plurality of portable devices relative to the user's body; and generating an electronic message by one or more of the plurality of portable devices instructing the user to position one or more of the plurality of portable devices relative to the user's body, in accordance with the one or more positions determined, for capturing a new plurality of signals generated by the one or more sensors in response to further sensor-detected movements of the user's body during one or more new respiratory cycles.

16. The computer program product of claim 13, wherein the program instructions are executable by the processor to cause the processor to initiate operations further comprising:

selecting from a plurality of breathing tests a breathing test for the user to perform with the plurality of portable devices, wherein the breathing test is selected based on a likelihood that meets or exceeds a predetermined probability level that, given the determined respiratory condition of the user, the user is capable of performing the breathing test; and determining one or more positions for the user to position one or more of the plurality of portable devices relative to the user's body based on the breathing test selected for the user to perform.

17. The computer program product of claim 13, wherein the plurality of portable devices comprises a first portable device and a second portable device, the first portable device positioned adjacent a chest portion of the user's body, and the second portable device position adjacent an abdominal portion of the user's body;

the first portable device generates a first time-based waveform by capturing a plurality of signals generated in response to sensor-detected movements of the chest portion of the user's body during the one or more respiratory cycles;

the second portable device generates a second time-based waveform by capturing a plurality of signals generated in response to sensor-detected movements of the abdominal portion of the user's body during the one or more respiratory cycles; and the program instructions are executable by the processor to cause the processor to initiate operations further comprising estimating breathing synchrony based on a phase difference between the first and second time-based waveforms and determining the respiratory condition of the user based on the estimated breathing synchrony.

* * * * *